(12) United States Patent
Wahlberg et al.

(10) Patent No.: US 7,651,853 B2
(45) Date of Patent: *Jan. 26, 2010

(54) CULTURES OF GFAP+ NESTIN+ CELLS THAT DIFFERENTIATE TO NEURONS

(75) Inventors: Lars Wahlberg, Asnaes (DK); Kenneth Campbell, Cincinnati, OH (US); Charlotta Skogh, Malmö (SE); Cecilia Eriksson, Falsterbo (SE); Klas Wictorin, Lund (SE)

(73) Assignee: NsGene A/S, Ballerup (DK)

( * ) Notice: Subject to any disclaimer, the term of this patent is extended or adjusted under 35 U.S.C. 154(b) by 40 days.

This patent is subject to a terminal disclaimer.

(21) Appl. No.: 11/932,349

(22) Filed: Oct. 31, 2007

(65) Prior Publication Data

US 2008/0138895 A1 Jun. 12, 2008

Related U.S. Application Data

(63) Continuation of application No. 11/062,886, filed on Feb. 22, 2005, now Pat. No. 7,303,912, which is a continuation of application No. 09/696,530, filed on Oct. 24, 2000, now Pat. No. 6,878,543.

(60) Provisional application No. 60/161,316, filed on Oct. 25, 1999.

(51) Int. Cl.
  *C12N 5/00* (2006.01)
  *C12N 5/02* (2006.01)
  *C12N 5/06* (2006.01)
  *C12N 5/08* (2006.01)

(52) U.S. Cl. ............ 435/325; 435/366; 435/368; 435/378

(58) Field of Classification Search ........ 435/325, 435/366, 368, 378
See application file for complete search history.

(56) References Cited

U.S. PATENT DOCUMENTS

| | | | | |
|---|---|---|---|---|
| 4,352,883 A | 10/1982 | Lim | ............ | 435/178 |
| 4,353,888 A | 10/1982 | Sefton | ............ | 424/25 |
| 4,968,733 A | 11/1990 | Müller et al. | ............ | 521/64 |
| 4,976,859 A | 12/1990 | Wechs | ............ | 210/500.23 |
| 5,071,741 A | 12/1991 | Brockbank | ............ | 435/1 |
| 5,084,350 A | 1/1992 | Chang et al. | ............ | 428/402.2 |
| 5,158,881 A | 10/1992 | Aebischer et al. | ............ | 435/182 |
| 5,284,761 A | 2/1994 | Aebischer et al. | ............ | 435/182 |
| 5,338,839 A | 8/1994 | McKay et al. | ............ | 536/235 |
| 5,750,376 A | 5/1998 | Weiss et al. | ............ | 435/69.52 |
| 5,753,506 A | 5/1998 | Johe | ............ | 435/377 |
| 5,766,948 A | 6/1998 | Gage et al. | ............ | 435/368 |
| 5,800,828 A | 9/1998 | Dionne et al. | ............ | 424/422 |
| 5,851,832 A | 12/1998 | Weiss et al. | ............ | 435/368 |
| 5,968,829 A | 10/1999 | Carpenter | ............ | 435/467 |
| 6,040,180 A | 3/2000 | Johe | ............ | 435/377 |
| 6,258,353 B1 | 7/2001 | Isacson et al. | ............ | 424/93.1 |
| 6,294,383 B1 | 9/2001 | Isacson et al. | ............ | 435/379 |
| 6,497,872 B1 | 12/2002 | Weiss et al. | ............ | 424/93.1 |
| 7,303,912 B2 * | 12/2007 | Wahlberg et al. | ............ | 435/325 |
| 2002/0151066 A1 | 10/2002 | Rubenstein et al. | ............ | 435/456 |
| 2003/0032181 A1 | 2/2003 | Weiss et al. | ............ | 435/368 |

FOREIGN PATENT DOCUMENTS

| WO | WO 92/04033 | 3/1992 |
|---|---|---|
| WO | WO 92/19195 | 11/1992 |
| WO | WO 93/14191 | 7/1993 |
| WO | WO 95/05452 | 2/1995 |
| WO | WO 95/07611 | 3/1995 |
| WO | WO 96/04368 | 2/1996 |
| WO | WO 96/09543 | 3/1996 |
| WO | WO 96/27287 | 7/1996 |
| WO | WO 96/29862 | 10/1996 |
| WO | WO 98/14058 | 4/1998 |
| WO | WO 98/30678 | 7/1998 |
| WO | WO 00/24897 | 5/2000 |

OTHER PUBLICATIONS

Björklund *Trends Neurosci.*, 14(8):319-322 (1991).
Brüstle et al. *Neuron*, 15:1275-1285 (1995).
Cunningham et al. *J. Neurosci. Meth.*, 47:105-114 (1993).
Daadi et al. *J. Neurosci.*, 19(11):4484-4497 (1999).
David et al. *J. Biol. Chem.*, 271(16):9185-9188 (1996).
Doetsch et al. *Cell*, 97(6):703-716 (1999).
Duncan et al. *J. Neurocytol.*, 17:351-360 (1988).
Eriksson et al. Eur. *J. Neurol.*, 12(Supp. 11):263 (2000).
Eriksson et al. *Exp. Neurol.*, 164:184-199 (2000).
Faaland et al. *Mol. Cell. Biol.*, 11(5):2697-2703 (1991).
Fagerström et al. *Eur. J. Neurol.*, 12(Supp. 11):326 (2000).
Fields et al. *J. Neuroimmunol.*, 8:311-330 (1985).
Gallo et al. *J. Neurosci.*, 15(1):394-406 (1995).
Gates et al. *Neurosci.*, 84(4):1013-1023 (1998).
Gruber *Transplantation*, 54(1):1-11 (1992).
Hammang et al. *Exp. Neurol.*, 147:84-95 (1997).
Hankin et al. *J. Comp. Neurol.*, 263:455-466 (1987).
Hulspas et al. *Experimental Neurol.*, 148(1):147-156 (1997).
Hunter-Schaedle *J. Neurobiol.*, 33:459-472 (1997).
Jessen et al. *J. Neurocytol.*, 13:923-934 (1984).
Johansson et al. *Cell*, 96(1):25-34 (1999).
Kalyani et al. *J. Neurosci.*, 18(19):7856-7868 (1998).

(Continued)

*Primary Examiner*—Ruth A Davis
(74) *Attorney, Agent, or Firm*—Mintz, Levin, Cohn, Ferris, Glovsky and Popeo, P.C.; Ivor Elrifi; Sheridan Snedden

(57) ABSTRACT

Cultures of cells immunoreactive for glial fibrillary acidic protein (GFAP), as well as for the intermediate filament marker nestin were grown in a medium including epidermal growth factor (EGF) and serum. The cultured cells had the morphology of astroglial cells. The cells can be proliferated in adherent or suspension cultures. Depending on the culture conditions, the cells can be induced to differentiate to neurons or glial cells. The cultures can be expanded over a large number of passages during several months, and survive, express an astroglial phenotype and integrate well after transplantation into both neonatal and adult rat forebrain.

27 Claims, 5 Drawing Sheets

OTHER PUBLICATIONS

Karlsson et al. *Biophys. J.*, 65:2524-2536 (1993).
Lagenaur et al. *J. Neurobiol.*, 23:71-88 (1992).
Lagenaur et al. *J. Supramol. Struct. Cell. Biochem.*, 15:335-346 (1981).
Lendahl et al. *Cell*, 60:585-595 (1990).
Lin et al. *Neurobiol. Dis.*, 2:79-85 (1995).
Lin, et al. *Hum. Gene Ther.*, 8:331-339 (1997).
Lundberg et al. *Exp. Neurol.*, 139:39-53 (1996).
Mi et al. *Dev. Brain Res.*, 106:145-154 (1998).
Misson et al. *Dev. Brain Res.*, 44:95-108 (1988).
Miyaguchi *J. Struct. Biol.*, 120(1):61-68 (1997).
Olsson et al. *Neurosci.*, 79(1):57-78 (1997).
Palmer et al. *Mol. Cell. Neurosci.*, 8:389-404 (1997).
Parmar et al. *Mol. Cell. Neurosci.*, 21:645-656 (2002).
Reynolds et al. *Dev. Biol.*, 175:1-13 (1996).
Reynolds et al. *J. Neurosci.*, 12(11):4565-4574 (1992).
Reynolds et al. *Science*, 255:1707-1710 (1992).
Ridet et al. *Hum. Gene Ther.*, 10:271-280 (1999).
Rutka et al. *Int. J. Dev. Neurosci.*, 17(5-6):503-515 (1999).
Santa-Olalla et al. *J. Neurosci. Res.*, 42(2):172-183 (1995).
Schinstine et al. *Edperimental Neurol.*, 141(1):67-78 (1996).
Skogh et al. *Neurosci.*, 120:379-385 (2003).
Stenman et al. *J. Neurosci.*, 23(1):167-174 (2003).
Svendsen et al. *Exp. Neurol.*, 148:135-146 (1997).
Tornatore et al. *Cell Transplant.*, 5(2):145-163 (1996).
Vescovi et al. *Exp. Neurol.*, 156:71-83 (1999).
Weiss et al. *J. Neurosci.*, 16(23):7599-7609 (1996).
Weiss et al. *Trends Neurosci.*, 19:387-393 (1996).
Wictorin et al. *Eur. J. Neurosci.*, 3:86-101 (1991).
Yong et al. *Proc. Nat. Acad. Sci. USA*, 88:7016-7020 (1991).
Zheng et al. *Proc. Natl. Acad. Sci. USA*, 88:8067-8071 (1991).
Zhou et al. *J. Comp. Neurol.*, 317:145-155 (1992).

* cited by examiner

CULTURES OF GFAP+ NESTIN+ CELLS THAT DIFFERENTIATE TO NEURONS

CLAIM OF PRIORITY

This application is a Continuation of U.S. application Ser. No. 11/062,886, filed Feb. 22, 2005 now U.S. Pat. No. 7,303,912, which is a Continuation of U.S. application Ser. No. 09/696,530, filed Oct. 24, 2000 now U.S. Pat. No. 6,878,543, which claims priority to U.S. provisional patent application 60/161,316, filed Oct. 25, 1999 the disclosures of which are incorporated herein by reference.

TECHNICAL FIELD OF THE INVENTION

This invention relates generally to glial cell cultures, and more particularly to methods and media for proliferating and differentiating GFAP+ nestin+ cells.

BACKGROUND OF THE INVENTION

The development of the mammalian central nervous system (CNS) begins in the early stage of embryonic development and continues until the post-natal period. The first step in neural development is cell birth, which is the precise temporal and spatial sequence in which neural stem cells and neural stem cell progeny (i.e. daughter neural stem cells and neural progenitor cells) proliferate. Proliferating cells give rise to neuroblasts, glioblasts, and new neural stem cells. The next step is a period of neural cell differentiation and migration, which give rise to the neurons and glial cells that migrate to their final positions. The neural component of the mature mammalian CNS is composed of neuronal cells (neurons) and glial cells (astrocytes and oligodendrocytes).

In mammals, specialized glial cells called radial glia develop immediately before the differentiation and migration of neurons. These radial glial cells span the cerebral wall from the ventricular surface of the neuroepithelium to the pial surface, forming a scaffolding for the initiation and maintenance of neuronal cell migration. Through a series of reciprocal signaling events between the migrating neurons and the radial glia, neurons migrate from their site of origin to their final position along the elongated processes of the radial glial cells. During neuronal migration, radial glial cells do not divide. After neuronal production and migration end, however, the radial glia enter a mitotic cycle, eventually differentiating into multipolar astrocytes. In lower vertebrates, radial glia has the capacity to form neurons but it is currently unclear whether radial glia or other types of glial precursors have the same capacity in mammals. Collectively, several studies suggest that may be only a small (and often reversible) transition between neuroepithelial stem cells and radial glia.

The use of cells for neural transplantation is well documented. Several studies have indicated that primary tissue from the developing ventral mesencephalon can give rise to dopaminergic neurons and supporting cells capable of survival, function, and therapeutic efficacy in Parkinson's patients. In addition, the transplantation of cultures containing neural precursor cells and stem cells can give rise all three major cell subtypes of the CNS, i.e. neurons, astrocytes, and oligodendrocytes. From these studies, there is a clear need in the art for cells capable of proliferating to make large numbers of cells as well as a capacity for neural differentiation in order to make the appropriate "adult" cells capable of integrating and restoring function to a diseased area in the CNS. Furthermore, over the past couple of decades, protein factors capable of protecting neural cells in the CNS from damage and capable of restoring function have bee discovered. From neuroprotection studies, it is evident that these protein factors may best work if delivered by gene manipulated cells placed in the area of disease. Thus, there is also a need in the art for transplantable neural cell lines capable of being gene modified in order to secrete protein factors locally. In addition, cell lines capable of making neurons and other neural lineages in a reproducible manner are useful screening targets to identify factors and drugs capable of influencing the CNS. Hence, there is a need in the art for neural cell lines for drug screening purposes. Last, with the human genome almost completely sequenced, there is a need for cells of neural lineages, which can be used to identify cDNA libraries to screen for gene function.

If glial precursor cells of the mammalian CNS could form neurons, astrocytes and perhaps other subtypes, a dividing pool of glial precursor cells could become a reliable source of large numbers of neural cells for the needs described above identifying several areas of industrial application. Preferably, cellular division in such glial precursor cells would be epigenetically regulated, so that a suitable number of glial precursor cells could be efficiently prepared in sufficient numbers for transplantation. However, these cells could also be genetically modified in order to be made to proliferate or differentiate in a reproducible manner. Furthermore, the cells could be genetically modified in order to produce a protein factor suitable as a therapeutic. The unmodified or gene modified glial precursor cells should be suitable in autografts, xenografts, and allografts as well as for in vitro use to screen for drug activity or gene expression. Protocols allowing for stable and long-term propagation of glial precursor cells would therefore be of great value. If such cultures could grow over extended periods, their properties would be interesting to compare to those of neural stem cells.

SUMMARY OF THE INVENTION

The invention provides glial precursor cultures of GFAP+ nestin+ cells with the potential to differentiate to neurons or glial cells, depending on the culture conditions chosen. These cells can be expanded using proliferation-inducing growth factor. Cells in cultures that have been expanded extensively express similar phenotypes to those passaged fewer times. Alternatively, these cells can be induced to make a significant number of neurons when placed under non-proliferating and serum-free conditions. These neurons show regional characteristics from their origin of isolation and will express those markers even after long-term culture. Moreover, these cells can make a significant number of astrocytes when placed under proliferating serum free conditions.

In one embodiment, cell cultures (for example, mouse or human) can be established from cells that have been isolated from the medial ganglionic eminence (MGE) and lateral ganglionic eminence (LGE). The cultured cells display glial morphology and both glial fibrillary acidic protein (GFAP) and nestin immunoreactivity. In this embodiment, the cell cultures contain cells that express the radial glial marker, RC-2. The cells are at least bi-potential and can make both non-mitotic GFAP+ astrocytes or non-mitotic beta-tubulin III+ neurons, depending on the culture conditions.

In another embodiment, EGF-stimulated and serum-containing long-term cultures of cells from the embryonic mouse lateral ganglionic eminence (LGE) can be expanded over many passages during several months, survive, express an astroglial phenotype and integrate well after transplantation into both neonatal and adult rat forebrain. Cells propagated in such cultures are interesting to compare and contrast with central nervous system (CNS) neural stem cells grown as neurospheres in EGF-stimulated cultures and are useful for studies of astroglial development and migration, and for use in trials with ex vivo gene transfer.

The invention provides a composition of a GFAP$^+$ nestin$^+$ cell in a culture medium supplemented with serum and at least one proliferation-inducing growth factor (for example, epidermal growth factor (EGF) and/or basic fibroblast growth factor (FGF-2) capable of undergoing neuronal differentiation.

The invention provides a method for the in vitro proliferation of neural cells, to produce large numbers of glial precursor cells available for transplantation that are capable of differentiating into neurons and into glial cells. The method includes the steps of (a) obtaining neural tissue from a mammal (e.g., from fetal tissue) (b) dissociating the neural tissue to obtain a cell suspension (c) culturing the cell in a culture medium containing a serum and a proliferation-inducing growth factor, (d) passaging the proliferated cultured cells. Proliferation and perpetuation of the GFAP$^+$ nestin$^+$ cells can be carried out either in suspension cultures or by allowing cells to adhere to a fixed substrate such as tissue coated plastic, polylysine, or laminin.

The invention also provides a method for the in vitro differentiation of the proliferated GFAP$^+$ nestin$^+$ cells to form neurons and glia. The invention also provides a method for making regionally specified neurons.

The invention provides a method for the in vivo transplantation of GFAP$^+$ nesting cells, which includes implanting the GFAP$^+$ nestin$^+$ cells that have been proliferated in vitro. Thus, the invention provides a means for generating large numbers of undifferentiated and differentiated neural cells for neurotransplantation into a host to treat neurodegenerative disease, neurological trauma, stroke, or in other diseases of the nervous system involving neuronal and glial cell loss or where normal function needs to be restored such as in metabolic or storage diseases. The invention also provides for methods of treating neurodegenerative disease and neurological trauma.

The invention provides a method for the transfection of GFAP$^+$ nestin$^+$ with vectors which can express the gene products for growth factors, growth factor receptors, and peptide neurotransmitters, or express enzymes, which are involved in the synthesis of neurotransmitters, including those for amino acids, biogenic amines and neuropeptides, and for the transplantation of these transfected cells into regions of neurodegeneration.

The invention provides a method of generating large numbers of neural cells for screening putative therapeutic agents targeted at the nervous system and for models of CNS development, function, and dysfunction. The invention also provides a method for the screening of potential neurologically therapeutic pharmaceuticals using GFAP$^+$ nestin$^+$ cells that have been proliferated in vitro. The invention further provides a cDNA library prepared from a GFAP$^+$ nestin$^+$ cell

DETAILED DESCRIPTION OF THE INVENTION

Figure 1:
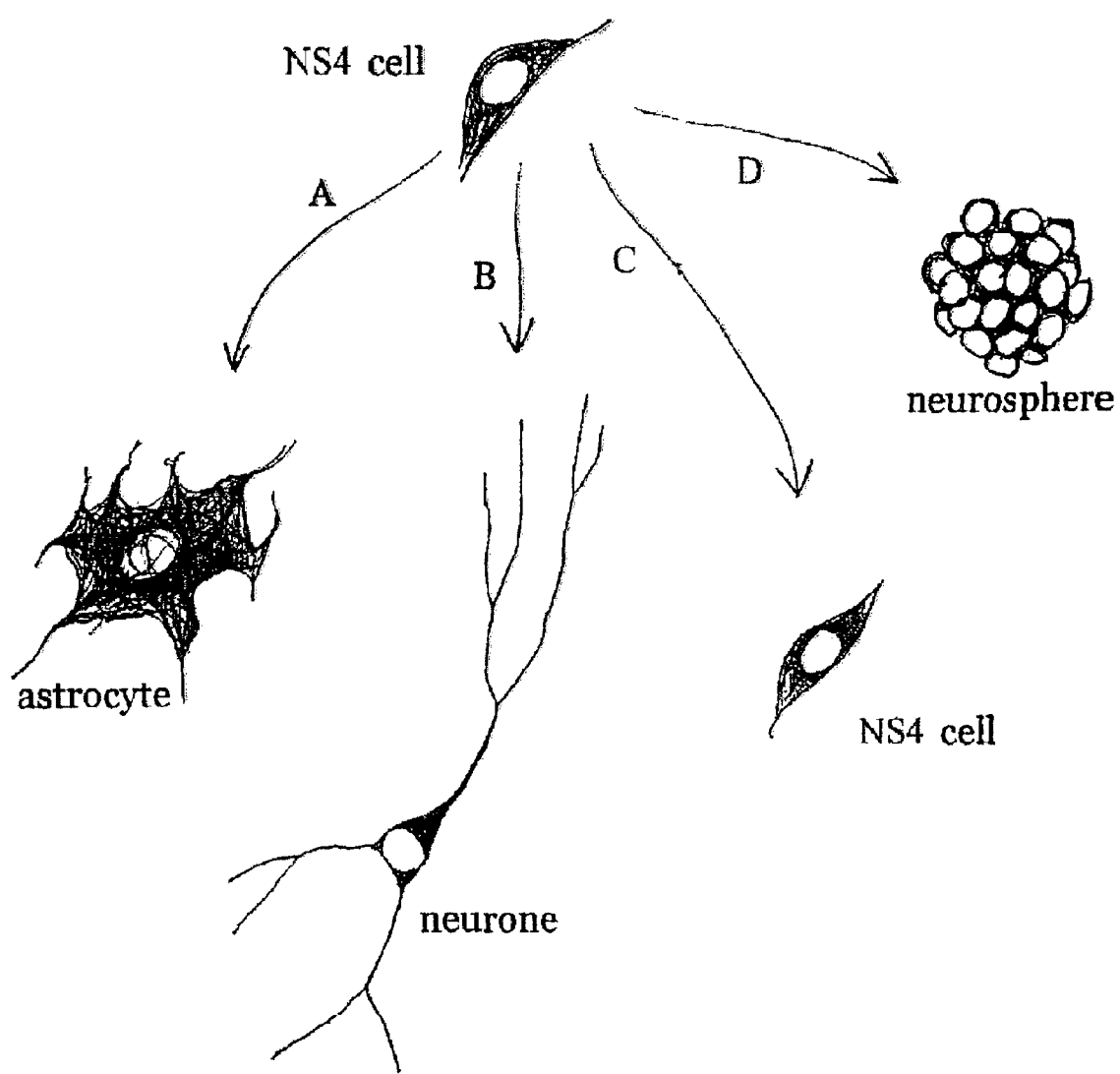
FIG. 1 illustrates the differentiation of a GFAP$^+$ nestin$^+$ cell to an astrocyte (A); the differentiation of a GFAP$^+$ nestin$^+$ cell to a neuron (B); the proliferation of GFAP$^+$ nestin$^+$ cells in suspension culture as neurospheres (C); or the proliferation of GFAP$^+$ nestin$^+$ cells in adherent culture (D).
Figure 2:
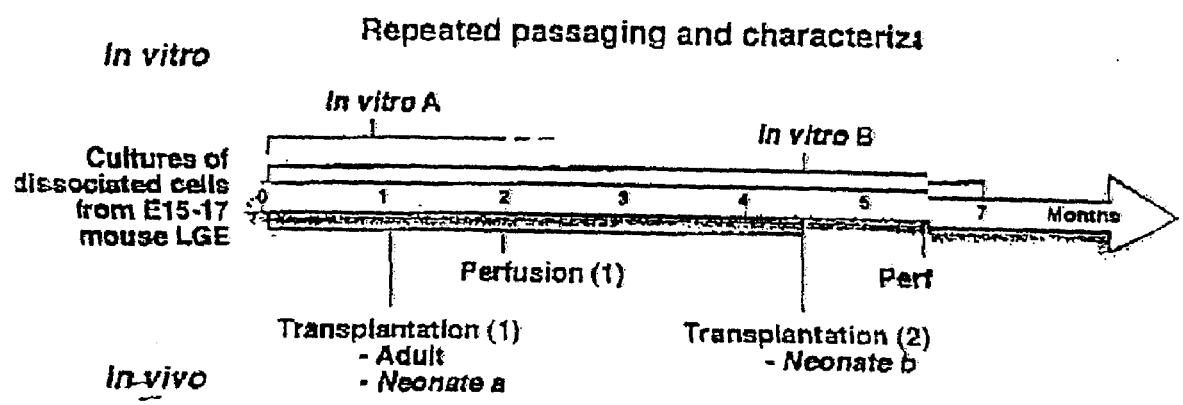
FIG. 2 illustrates, the in vitro and in vivo procedures of the invention.

GFAP$^+$ Nestin$^+$ cells. The invention provides "NS4" cells. An NS4 cell is an undifferentiated neural cell that can be induced to proliferate using the methods of the present invention. The NS4 cell is capable of self-maintenance, such that with each cell division, at least one daughter cell will also be a NS4 cell. A NS4 cell has a glial morphology and is immunoreactive for both glial fibrillary acidic protein (GFAP) and nestin.

Glial fibrillary acidic protein (GFAP) is an intermediate filament protein specifically expressed by astrocytes and glial cells of the central nervous system and by Schwann cells, the glial cells of the peripheral nervous system (Jessen et al., 13 J. Neurocytology 923-934 (1984) and Fields et al., 8 J. Neuroimmunol. 311-330 (1989)). Anti-GFAP antibodies are commercially available (e.g., a rabbit monoclonal antibody raised against GFAP is available from DAKO).

Nestin is an intermediate filament protein found in many types of undifferentiated CNS cells. During neurogenesis and gliogenesis, nestin is replaced by cell type-specific intermediate filaments, e.g. neurofilaments and glial fibrillary acidic protein (GFAP). The nestin marker was characterized by Lendahl et. al., 60 Cell 58.5-595 (1990). Antibodies are available to identify; nestin, including the rat antibody. Rat401.

The co-expression of GFAP and nestin is compatible with the NS4 cells being a population of astroglial cell precursors. Dividing cells cultured from neonatal rat cerebral cortex, with a typical morphology of type I astroglial cells, co-express GFAP and nestin (Gallo et al., 15 J. Neurosci 394-406 (1995)). Also reactive astrocytes surrounding an ischemic or mechanical lesion site co-express GFAP and nestin (Lin et al., 2 Neurobiol. Dis. 79-85 (1995)). The properties of GFAP$^+$ nestin$^+$NS4 cells, which can be grown long-term and repeatedly passaged cultures, are also interesting in the light of recent publications describing the existence of GFAP$^+$ cells in the ependymal or subependymal zones (Doetsch et al., 97 Cell 703-16 (1999), Johansson et al., 96 Cell 25-34 (1999)) which are the areas containing actively dividing neural stem and precursor cells.

NS4 cells can be obtained from embryonic neural tissue. The neural tissue can be obtained from any animal that has neural tissue such as insects, fish, reptiles, birds, amphibians, mammals and the like. The preferred source neural tissue is from mammals, preferably rodents and primates, and most preferably, mice (see, EXAMPLE 1) and humans (see, EXAMPLE 2).

When NS4 cells are obtained from a heterologous donor, the donor may be euthanized, and the neural tissue and specific area of interest removed using a sterile procedure. Areas of interest are any area from which NS4 cells can be obtained that can serve to restore function to a degenerated area of the host's nervous system, particularly the host's CNS. Suitable areas include the medial ganglionic eminence and the lateral ganglionic eminence. Autologous neural tissue can be obtained by biopsy, or from patients undergoing neurosurgery in which neural tissue is removed, for example, during epilepsy surgery, temporal lobectomies and hippocampectomies. Human heterologous NS4 cells can be derived from embryonic or fetal tissue following elective abortion (EXAMPLE 2), or from a post-natal, juvenile or adult organ donor.

The present invention provides an alternative way to generate enriched populations of astroglial cells from different regions. The NS4 cells resemble type I astroglial cells both in vitro and following implantation. An interesting migration pattern was observed in the neonatal recipients, with cells migrating along the internal capsule into the globus pallidus and some other adjacent structures, whereas, when the grafts were placed into adult recipients, they remained mostly around the injection site, with only limited migration into the adjacent striatum (see, EXAMPLE 7).

While neurons and glia were present in the dissociated cell culture, after several passages, the cultures are severely deficient of cells possessing neuronal morphologies or expressing neuronal markers. These cultures are highly enriched in cells having GFAP and nestin immunoreactivity and expressing glial morphology. The cell cultures also contain cells expressing the radial glial marker RC2.

NS4 cells can be maintained in vitro in long-term cultures. Cells from the embryonic mouse lateral ganglionic eminence (LGE) were grown in attached, epidermal growth factor (EGF) stimulated and 10% serum-containing cultures, with around 90% GFAP$^+$ nestin$^+$ cells, over repeated passages during several months. After a gradual decline in division rate during the first 6-8 passages, the cultures thereafter propagated readily again, with a stable and high growth rate, for at least seven months. Cells grew as attached GFAP$^+$ nestin$^+$ cells with an astroglial-like morphology (see EXAMPLE 4).

The cultured mouse NS4 cells were also positive for the mouse-specific neural antibodies M2 (Lagenaur & Schachner, 15 J. Supramol. Struct. Cell Biochem. 335-46 (1981)) and M6 (Lagenaur et al., 23 J. Neurobiol. 71-88 (1992)). Although M2 has been found to label both glial and neuronal cell surfaces, in cerebellar monolayer cultures and in cerebellar tissue sections (Lagenaur & Schachner, 15 J. Supramol. Struct. Cell Biochem. 335-46 (1981)), several in vivo studies have characterized the M2 antibody as a reliable marker for astroglial cells (Zhou & Lund, 317 J. Comp. Neurol. 145-55 (1992)). M6 is a neuronal cell surface glycoprotein with unknown function (Mi et al., 106 Dev. Brain Res. 145-54 (1998); Lagenaur et al., 23 J. Neurobiol. 71-88 (1992); Hankin & Lund, 263 J. Comp. Neurol. 45 5-66 (1987); Wictorin et al., 3 Eur. J. Neurosci. 86-101 (1991)). Several in vivo studies have shown that M6 can also be expressed on glial cells (Mi et al., 106 Dev. Brain Res. 145-54 (1998)). The M6-immunoreactivity is observed in the majority of the cultured NS4 cells and therefore does not indicate that the cells have certain neuronal characteristics. The M2 and M6 staining patterns were clearly similar to those of GFAP and nestin, with the vast majority of the cells immunopositive for all of these four markers, at both early and late passages.

In addition, some NS4 cells show immunoreactivity for the radial glia marker RC-2. RC2 is a monoclonal antibody that specifically recognizes a radial glial cell antigen that is expressed at varying amounts during CNS development. There is a high level of expression during embryonic brain development, lower levels in early postnatal transitional glia, and none in astrocytes after the second postnatal week. Hunter et al., 33 J. Neurobiol. 459-472 (1997); Mission et al., 44 Dev. Brain Res. 95-108 (1988).

NS4 cells were negative when stained for neuronal markers, such as, beta-III tubulin or NeuN. Antibodies recognizing, beta-tubulin isotype III (beta-III-tubulin) are commercially available (for example, mouse monoclonal antibodies from Sigma Chemicals, St. Louis Mo.). Antibody to Neuro-Specific Nuclear Protein (NeuN) reacts with most neuronal cell types throughout the nervous system, is available from Chemicon (Temecula Calif.). The antibody is neuron-specific; no staining of glia is observed. Other neuronal markers include the homeobox-related murine gene MEIS2 labels the lateral somitic compartment and derivatives during early mouse embryogenesis and later becomes a marker for the dorso-ectodermal region, overlying cells of the paraxial mesoderm. MEIS2 is also highly expressed in specific areas of the developing central nervous system from embryonic day 9 (E9) onward. In later developmental stages, a strong expression is detectable in differentiating nuclei and regions of the forebrain, midbrain, hindbrain, and spinal cord. (see, Toresson et al., 126 (6) Development 13 17-1326 (1999)). Another neuronal marker is the DLX homeobox gene, which is expressed in distinct regions of the embryonic forebrain, including the striatum, neocortex and retina (see, Eisenstat et al., 414(2) J. Comp. Neurol. 2 17-37 (1999))

NS4 cells survive transplantation into neonatal or adult animal striatum, with astroglia-like properties for the implanted cells, and good integration and migration, especially in the neonatal recipients. Transplantation of astroglial cells is today a widely used method for in vivo studies of astroglial cells during development and in regeneration, often with the cells grafted as a component of primary tissue, with a mix of different precursor cells. To determine specific properties of the astroglial cells, it is however interesting to be able to acquire relatively-pure cell populations.

Contrast between NS4 cells of the invention and CNS neural stem cells. The NS4 cells of the invention are similar to and yet different from CNS neural stem cells. Neurobiologists have used various terms interchangeably to describe the undifferentiated cells of the CNS. Terms such as "stem cell", "precursor cell" and "progenitor cell" are commonly used in the scientific literature to describe different types of undifferentiated neural cells, with differing characteristics and fates. One approach to obtain CNS neural stem cells is to trophic factor-stimulate and grow neural stem (or progenitor) cells in the form of neurospheres (see, U.S. Pat. Nos. 5,750,376 and 5,851,832, to Weiss et al. U.S. Pat. No. 5,753,506, to Johe, U.S. Pat. No. 5,968,829, to Carpenter (all incorporated herein by reference), Weiss et al., 19 Trends Neurosci. 387-93 (1996); Reynolds et al, 12 J. Neurosci. 4565-74 (1992), Reynolds & Weiss, 255 Science 1707-10 (1992); Reynolds & Weiss, 175 Dev. Biol. 1-13 (1996)). Indeed, such precursor cells derived from, for instance, the embryonic or adult rodent or human forebrain, can be grown and multiplied as non-attached neurospheres over long periods, in a serum-free medium including EGF. In vitro, cells in the neurospheres differentiate into neurons, astrocytes or oligodendrocytes, when plated onto an adhesive substrate.

Cells isolated from the embryonic (or adult) mouse striatum can proliferate in response to EGF-stimulation and grow in a medium without serum, as non-attached clusters or spheres of clonally derived undifferentiated progenitor/stem cells, but with a potential to differentiate into neurons, astrocytes or oligodendrocytes. EGF-expanded neurospheres are nestin$^+$ but GFAP$^-$. Upon transplantation into the CNS, the neurospheres give rise to neuronal, glial, and nonneural cells and are capable of differentiating into various neurons such as hippocampal neurons of the granule cell layer and olfactory interneurons (Hammang et al., 147 Exp. Neurol. 84-95 (1997); Winkler et al., 11 Mol. Cell. Neurosci. 99-116 (1998)); Fricker et al., 19 J. Neurosci. 5990-6005 (1999), Svendsen et al., 148 Exp. Neurol. 135-46 (1997), and Vescovi et al., 156 Exp. Neurol. 71-83 (1999)). NS4 cells appear to be more restricted and retain their regional specification and, for example, cells differentiated from precursors derived from the LGE and propagated for multiple passages expressed striatal neuronal markers such as MEIS2 and DLX1 and did not express markers of cortical or medial ganglionic eminence neuronal precursors (see EXAMPLE 5).

Culture conditions. NS4 cells can be proliferated using the methods described herein. Cells can be obtained from donor tissue by dissociation of individual cells from the connecting extracellular matrix of the tissue (see, EXAMPLES 1-2). Tissue from a particular neural region is removed from the brain using a sterile procedure, and the cells are dissociated using any method known in the art including treatment with enzymes such as trypsin, collagenase and the like, or by using physical methods of dissociation such as with a blunt instrument or homogenizer. Dissociation of fetal cells can be carried out in tissue culture medium. Dissociation of juvenile and adult cells can be carried out in 0.1% trypsin and 0.05% DNase in DMEM. Dissociated cells are centrifuged at low speed, between 200 and 2000 rpm, usually between 400 and 800 rpm, and then resuspended in a culture medium. The neural cells can be cultured in suspension or on a fixed substrate. Dissociated cell suspensions are seeded in any receptacle capable of sustaining cells, particularly culture flasks, culture plates or roller bottles, and more particularly in small culture flasks such as 25 cm$^2$ culture flasks. Cells cultured in suspension are resuspended at approximately $5 \times 10^4$ to $2 \times 10^5$ cells/ml (for example, $1 \times 10^5$ cells/ml). Cells plated on a fixed substrate are plated at approximately $2-3 \times 10^3$ 10 cells/cm$^2$ (for example, $2.5 \times 10^3$ cells/cm$^2$).

The dissociated neural cells can be placed into any known culture medium capable of supporting cell growth, including HEM, DMEM, RPMI, F-12, and the like, containing supplements which are required for cellular metabolism such as glutamine and other amino acids, vitamins, minerals and proteins such as transferrin and the like. The culture medium may also contain antibiotics to prevent contamination with yeast, bacteria and fungi such as penicillin, streptomycin, gentamicin and the like. The culture medium may contain serum derived from bovine, equine, chicken and the like.

In one embodiment, the invention provides a culture medium for the proliferation of NS4 cells. The medium is a defined culture medium containing a mixture of DMEM/F12, supplemented with N2 (Gibco), and fetal calf serum. This culture medium is referred to as "NS4 Complete Medium" and is described in detail in EXAMPLE 1.

Conditions for culturing should be close to physiological conditions. The pH of the culture medium should be close to physiological pH. (for example, between pH 6-8, between about pH 7 to 7.8, or at pH 7.4). Physiological temperatures range between about 30° C. to 40° C. NS4 cells can be cultured at temperatures between about 32° C. to about 38° C. (or example, between about 35° C. to about 37° C.).

The culture medium is supplemented with at least one proliferation-inducing ("mitogenic") growth factor. A "growth factor" is protein, peptide or other molecule having a growth, proliferation-inducing, differentiation-inducing, or trophic effect on NS4 cells. "Proliferation-inducing growth factors" are trophic factor that allows NS4 cells to proliferate, including any molecule that binds to a receptor on the surface of the cell to exert a trophic, or growth-inducing effect on the cell. Proliferation-inducing growth factors include EGF, amphiregulin, acidic fibroblast growth factor (aFGF or FGF-1), basic fibroblast growth factor (bFGF or FGF-2), transforming growth factor alpha (TGFα), and combinations thereof. EGF is a known proliferation-inducing growth factor for astroglial cells (Simpson et al., 8 J. Neurosci. Res. 453-62 (1982)), and is also used in media for the propagation of CNS neural stem cells (Reynolds & Weiss, 255 Science 1707-10 (1992)). The combination of the EGF-containing neurosphere growth medium with the addition of serum gives rise to readily propagating attached cultures with high proportions of GFAP$^+$ cells.

Growth factors are usually added to the culture medium at concentrations ranging between about 1 fg/ml to 1 mg/ml. Concentrations between about 1 to 100 ng/ml are usually sufficient. Simple titration assays can easily be performed to determine the optimal concentration of a particular growth factor.

The biological effects of growth and trophic factors are generally mediated through binding to cell surface receptors. The receptors for a number of these factors have been identified and antibodies and molecular probes for specific receptors are available. NS4 cells can be analyzed for the presence of growth factor receptors at all stages of differentiation. In many cases, the identification of a particular receptor provides guidance for the strategy to use in further differentiating the cells along specific developmental pathways with the addition of exogenous growth or trophic factors.

Generally, after about 3-10 days in vitro, and more particularly after about 6-7 days in vitro, the proliferating NS4 cells are fed every 2-7 days (for example, every 2-4 days by aspirating the medium, and adding fresh "NS4 Complete Medium" containing a proliferation-inducing growth factor to the culture flask).

The NS4 cell culture can be easily passaged to reinitiate proliferation. After 6-7 days in vitro, the culture flasks are shaken well and NS4 cells The NS4 cells are then transferred to a 50 ml centrifuge tube and centrifuged at low speed. The medium is aspirated, the NS4 cells are resuspended in a small amount of "NS4 Complete Medium" with growth factor The cells are then counted and replated at the desired density to reinitiate proliferation. This procedure can be repeated weekly to result in a logarithmic increase in the number of viable cells at each passage. The procedure is continued until the desired number of NS4 cells is obtained.

NS4 cells and NS4 cell progeny can be cryopreserved by any method known in the art until they are needed. (See, e.g., U.S. Pat. No. 5,071,741, PCT International patent applications WO†93/14191, WO†95/07611, WO†96/27287, WO†96/29862, and WO†98/14058, Karlsson et al., 65 Biophysical J. 2524-2536 (1993)). The NS4 cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15% (for example, 8-10%). Cells are frozen gradually to a temperature of −10° C. to −150° C. (for example, −20° C. to −100° C., or −70° C. to −80° C.).

Differentiation of NS4 Cells. Depending on the culture conditions, NS4 cells can be differentiated into neurons and glial cells.

N54 cells can be differentiated into neurons by culturing the N54 cells on a fixed substrate in a culture medium that is free of the proliferation-inducing growth factor and serum. After removal of the proliferation-inducing growth factor and the serum, the N54 cells begin to differentiate into neurons. At this stage the culture medium may contain serum such as 0.5-1.0% fetal bovine serum (FBS). However, if defined conditions are required, serum is not used. Within 2-3 days, many of the N54 cell progeny begin to lose immunoreactivity for GFAP and nestin and begin to express antigens specific for neurons (e.g., β-tubulin III). Under the same conditions, N54 cells can be differentiated into mature astrocytes by culturing the cells on a fixed substrate in a culture medium that is free or deficient of serum. After removal of the serum, the cells flatten, and begin to differentiate into glia. Cells exhibit the astroglial morphology and lose immunoreactivity for nestin and begin to express GFAP in a fibrillary pattern characteristic for astrocytes.

Differentiation of the NS4 cells can also be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Instead of proliferation-inducing growth factors for the proliferation of NS4 cells (see above), differentiation-inducing growth factors can be added to the culture medium to influence differentiation of the NS4 cells. Differentiation inducing growth factors include NGF, platelet-derived growth factor (PDGF), thyrotropin releasing hormone (TRH), transforming growth factor betas (TGF), insulin-like growth factor (IGF-1) and the like.

Differentiated neuronal and glia cells can be detected using immunocytochemical techniques know in the art. Immunocytochemistry (e.g. dual-label immunofluorescence and immunoperoxidase methods) uses antibodies that detect cell proteins to distinguish the cellular characteristics or phenotypic properties of neurons from glia. Cellular markers for neurons include NSE, NF, β-tubulin, MAP-2 and NeuN. Cellular markers for glia include GFAP (an identifier of astrocytes), RC-2 (an identifier of radial glia) and M2.

Immunocytochemistry can also be used to identify neurons, by detecting the expression of neurotransmitters or the expression of enzymes responsible for neurotransmitter synthesis. For the identification of neurons, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or antidiuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins and enkephalins, prostaglandins, amino acids such as GABA, glycine, glutamate, cysteine, taurine and aspartate, and dipeptides such as carnosine. Antibodies to neurotransmitter-synthesizing enzymes can also be used such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors, the dopamine receptor, and the like. Cells that contain a high level of melanin, such as those found in the substantia nigra, could be identified using an antibody to melanin.

In situ hybridization histochemistry can also be performed, using cDNA or RNA probes specific for the peptide neurotransmitter or the neurotransmitter synthesizing enzyme mRNAs. These techniques can be combined with immunocytochemical methods to enhance the identification of specific phenotypes. If necessary, the antibodies and molecular probes discussed above can be applied to Western and Northern blot procedures respectively to aid in cell identification.

Transplantation of NS4 Cells. Transplantation of new cells into the damaged CNS has the potential to repair damaged neural pathways and provide neurotransmitters, thereby restoring neurological function. However, the absence of suitable cells for transplantation purposes has prevented the full potential of this procedure from being met. "Suitable" cells are cells that meet the following criteria: (1) can be obtained in large numbers; (2) can be proliferated in vitro to allow insertion of genetic material, if necessary; (3) capable of surviving indefinitely but stop growing after transplantation to the brain; (4) are non-immunogenic, preferably obtained from a patient's own tissue or from a compatible donor; (5) are able to from normal neural connections and respond to neural physiological signals (Björklund, 14(8) Trends Neurosci. 319-322 (1991). The NS4 cells obtainable from embryonic or adult CNS tissue, which are able to divide over extended times when maintained in vitro using the culture conditions described herein, meet all of the desirable requirements of cells suitable for neural transplantation purposes and are a particularly suitable cell line as the cells have not been immortalized and are not of tumorigenic origin. The use of NS4 cells in the treatment of neurological disorders and CNS damage can be demonstrated by the use of animal models.

NS4 cells can be administered to any animal with abnormal neurological or neurodegenerative symptoms obtained in any manner, including those obtained as a result of mechanical, chemical, or electrolytic lesions, as a result of aspiration of neural areas, or as a result of aging processes. Lesions in non-human animal models can be obtained with 6-hydroxydopamine (6-OHDA), 1-methyl-4-phenyl-1,2,3,6 tetrahydropyridine (MPTP), ibotenic acid, and the like.

NS4 cells can be prepared from donor tissue that is xenogeneic to the host. For xenografts to be successful, some method of reducing or eliminating the immune response to the implanted tissue is usually employed. Thus NS4 cell recipients can be immunosuppressed, either through the use of immunosuppressive drugs such as cyclosporin, or through local immunosuppression strategies employing locally applied immunosuppressants. Local immunosuppression is disclosed by Gruber, 54 Transplantation 1-11 (1992). U.S. Pat. No. 5,026,365 discloses encapsulation methods suitable for local immunosuppression.

As an alternative to employing immunosuppression techniques, methods of gene replacement or knockout using homologous recombination in embryonic stem cells, taught by Smithies et al., 317 Nature 230-234 (1985), and extended to gene replacement or knockout in cell lines (Zheng et al., 88 Proc. Natl. Acad. Sci. 8067-8071 (1991)), can be applied to NS4 cells for the ablation of major histocompatibility complex (MHC) genes. NS4 cells lacking MHC expression allows for the grafting of enriched neural cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 Transplantation 1-11(1992). Exemplary approaches to the reduction of immunogenicity of transplants by surface modification are disclosed by PCT International patent application WO 92/04033 and PCT/US99/24630. Alternatively the immunogenicity of the graft may be reduced by preparing NS4 cells from a transgenic animal that has altered or deleted MHC antigens.

NS4 cells can be encapsulated and used to deliver factors to the host, according to known encapsulation technologies, including microencapsulation (see, e.g., U.S. Pat. Nos. 4,352,883; 4,353,888; and 5,084,350, herein incorporated by reference) and macroencapsulation (see, e.g., U.S. Pat. Nos. 5,284,761, 5,158,881, 4,976,859 and 4,968,733 and PCT International patent applications WO 92/19195 and WO 95/05452, each incorporated herein by reference). If the cells are encapsulated, we prefer macroencapsulation, as described in U.S. Pat. Nos. 5,284,761; 5,158,881; 4,976,859; 4,968,733; 5,800,828 and PCT International patent application WO 95/05452, each incorporated herein by reference. Cell number in the devices can be varied; preferably each device contains between $10^3$-$10^9$ cells (for example, $10^5$ to $10^7$ cells). Many macroencapsulation devices can be implanted in the host; we prefer between one to 10 devices.

NS4 cells prepared from tissue that is allogeneic to that of the recipient can be tested for use by the well-known methods of tissue typing, to closely match the histocompatibility type of the recipient.

NS4 cells can sometimes be prepared from the recipient's own nervous system (e.g., in the case of tumor removal biopsies). In such instances the NS4 cells can be generated from dissociated tissue and proliferated in vitro using the methods described above. Upon suitable expansion of cell numbers, the NS4 cells may be harvested, genetically modified if necessary, and readied for direct injection into the recipient's CNS.

Transplantation can be done bilaterally, or, in the case of a patient suffering from Parkinson's Disease, contralateral to the most affected side. Surgery is performed in a manner in which particular brain regions may be located, such as in relation to skull sutures, particularly with a stereotaxic guide. NS4 cells are delivered throughout any affected neural area, in particular to the basal ganglia, the caudate, the putamen, the nucleus basalis or the substantia nigra. Cells are administered to the particular region using any method which maintains the integrity of surrounding areas of the brain, such as by injection cannula. Injection methods are exemplified by those used by Duncan et al., 17 J. Neurocytology 351-361 (1988), and scaled up and modified for use in humans. Methods taught by Gage et al., supra, for the injection of cell suspensions such as fibroblasts into the CNS can also be used for injection of NS4 cells. Additional approaches and methods may be found in *Neural Grafting in the Mammalian CNS*, Björklund & Stenevi, eds. (1985).

NS4 cells administered to the particular neural region can form a neural graft, so that the cells form normal connections with neighboring neurons, maintaining contact with transplanted or existing glial cells, and providing a trophic influence for the neurons. Thus the transplanted NS4 cells re-establish the neuronal networks which have been damaged due to disease and aging.

Survival of the NS4 cell graft in the living host can be examined using various non-invasive scans such as computerized axial tomography (CAT scan or CT scan), nuclear magnetic resonance or magnetic resonance imaging (NMR or MRI), or positron emission tomography (PET) scans. Post-mortem examination of graft survival can be done by removing the neural tissue, and examining the affected region macroscopically and microscopically. Cells can be stained with any stains visible under light or electron microscopic conditions, more particularly with stains that are specific for neurons and glia. Particularly useful are monoclonal antibodies that identify neuronal cell surface markers such as the M6 antibody that identifies mouse neurons. Also useful are antibodies that identify neurotransmitters (such as GABA, TH, ChAT, and substance P) and to enzymes involved in the synthesis of neurotransmitters (such as GAD). Transplanted cells can also be identified by prior incorporation of tracer dyes such as rhodamine-labeled or fluorescein-labeled microspheres, fast blue, bisbenzamide, or retrovirally introduced histochemical markers such as the lacZ gene, which produces, $\alpha$-galactosidase.

Functional integration of the graft into the host's neural tissue can be assessed by examining the effectiveness of grafts on restoring various functions, including but not limited to tests for endocrine, motor, cognitive and sensory functions. Motor tests that can be used include those that measure rotational movement away from the degenerated side of the brain, and those that measure slowness of movement, balance, coordination, akinesia or lack of movement, rigidity and tremors. Cognitive tests include various tests of ability to perform everyday tasks, as well as various memory tests, including maze performance.

The ability to expand NS4 cells in vitro for use in transplantation is also useful for ex vivo gene therapy. For instance, rat primary astroglial cells (Lundberg et al., 139 Exp. Neurol. 39-53 (1996) or a human astroglial cell line (Tornatore et al., 5 Cell Transplant 145-63 (1996)) have been transduced with the tyrosine hydroxylase gene and implanted in models of Parkinsonis disease. More recently, astroglial cells for ex vivo gene therapy have also been derived from adult human cortex (Ridet et al., 10 Hum. Gene Ther. 27 1-80 (1999)). Thus, NS4 cells provide an additional way to retrieve and expand astroglial cells for use as vehicles in ex vivo gene therapy trials.

Genetic Modification of NS4 Cells. Although the NS4 cells are non-transformed primary cells, they possess features of a continuous cell line. In the undifferentiated state, the NS4 cells continuously divide and are thus targets for genetic modification. In some embodiments, the genetically modified cells are induced to differentiate into neurons or glia by any of the methods described above.

The term "genetic modification" refers to the stable or transient alteration of the genotype a of a NS4 cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Any useful genetic modification of the cells is within the scope of the present invention. For example, NS4 cells may be modified to produce or increase production of a biologically active substance such as a neurotransmitter or growth factor or the like. In one embodiment the biologically active substance is a transcription factor such as a transcription factor that modulates genetic differentiation, e.g., Nurr-1. In an alternative embodiment the biologically active substance is a non-mitogenic proliferation factor, e.g. v-myc, SV-40 large T or telomerase.

The genetic modification can be performed either by infection with viral vectors (retrovirus, modified herpes viral, herpes-viral, adenovirus, adeno-associated virus, and the like) or transfection using methods known in the art (lipofection, calcium phosphate transfection, DEAE-dextran, electroporation, and the like) (see, Maniatis et al., in *Molecular Cloning: A Laboratory Manual* (Cold Spring Harbor Laboratory, N.Y., 1982). For example, the chimeric gene constructs can contain viral, for example retroviral long terminal repeat (LTR), simian virus 40 (SV40), cytomegalovirus (CMV); or mammalian cell-specific promoters such as tyrosine hydroxylase (TH, a marker for dopamine cells), DBH, phenylethanolamine N-methyltransferase (PNMT), ChAT, GFAP, NSE, the NF proteins (NE-L, NF-M, NF-H, and the like) that direct the expression of the structural genes encoding the desired protein. In addition, the vectors can include a drug selection marker, such as the *E. coli* aminoglycoside phosphotransferase gene, which when co-infected with the test gene confers resistance to geneticin (G418), a protein synthesis inhibitor.

NS4 cells can be genetically modified using transfection with expression vectors. In one protocol, vector DNA containing the genes are diluted in 0.1×TE (1 mM Tris pH 8.0, 0.1 mM EDTA) to a concentration of 40 µg/ml. 22 µl of the DNA is added to 250 µl of 2×HBS (280 mM NaCl, 10 mM KCl, 1.5 mM $Na_2HPO_4$, 12 mM dextrose, 50 mM HEPES) in a disposable, sterile 5 ml plastic tube. 31 µl of 2 M $CaCl_2$ is added slowly and the mixture is incubated for 30 minutes (min) at room temperature. During this 30 min incubation, the cells are centrifuged at 800 g for 5 min at 4° C. The cells are resuspended in 20 volumes of ice-cold PBS and divided into aliquots of $1 \times 10^7$ cells, which are again centrifuged. Each aliquot of cells is resuspended in 1 ml of the DNA-$CaCl_2$ suspension, and incubated for 20 min at room temperature. The cells are then diluted in growth medium and incubated for 6-24 hr at 37° C. in 5%-7% $CO_2$. The cells are again centrifuged, washed in PBS and returned to 10 ml of growth medium for 48 hr.

NS4 cells can also be genetically modified using calcium phosphate transfection techniques. For standard calcium phosphate transfection, the cells are mechanically dissociated into a single cell suspension and plated on tissue culture-treated dishes at 50% confluence (50,000-75,000 cells/$cm^2$) and allowed to attach overnight. In one protocol, the modified calcium phosphate transfection procedure is performed as follows: DNA (15-25 µg) in sterile TE buffer (10 mM Tris, 0.25 mM EDTA, pH 7.5) diluted to 440 µL with TE, and 60 µL of 2 M $CaCl^2$ (pH to 5.8 with 1M HEPES buffer) is added to the DNA/TE buffer. A total of 500 µL of 2×HBS (HEPES-Buffered saline; 275 mM NaCl, 10 mM KCl, 1.4 mM $Na_2HPO_4$, 12 mM dextrose, 40 mM HEPES buffer powder, pH 6.92) is added dropwise to this mix. The mixture is allowed to stand at room temperature for 20 mm. The cells are washed briefly with 1×HBS and 1 ml of the calcium phosphate precipitated DNA solution is added to each plate, and the cells are incubated at 37° C. for 20 mm. Following this incubation, 10 ml of "NS4 Complete Medium" is added to the cells, and the plates are placed in an incubator (37° C., 9.5% $CO_2$) for an additional 3-6 hours. The DNA and the medium are removed by aspiration at the end of the incubation period, and the cells are washed 3 times with "NS4 Complete Growth Medium" and then returned to the incubator.

When the genetic modification is for the production of a biologically active substance, the substance can be one that is useful for the treatment of a given CNS disorder. NS4 cells can be genetically modified to express a biologically active agent, such as growth factors, growth factor receptors, neurotransmitters, neurotransmitter synthesizing genes, neuropeptides, and chromaffin granule amine transporter. For example, it may be desired to genetically modify cells so they secrete a proliferation-inducing growth factor or a differentiation-inducing growth factor. Growth factor products useful in the treatment of CNS disorders include NGF, BDNF, the neurotrophins, CNTF, amphiregulin, FGF-1, FGF-2, EGF, TGFα, TGF, PDGF, JGFs, and the interleukins.

Cells can also be modified to express a certain growth factor receptor (r) including, but not limited to, p75 low affinity NGF receptor, CNTF receptor, the trk family of neurotrophin receptors (trk, trkB, trkC), EGFr, FGFr, and amphiregulin receptors. Cells can be engineered to produce various neurotransmitters or their receptors such as serotonin, L-dopa, dopamine, norepinephrine, epinephrine, tachykinin, substance P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, CHAT, and histidine decarboxylase. Genes that encode for various neuropeptides, which may prove useful in the treatment of CNS disorders, include substance-P, neuropeptide-Y, enkephalin, vasopressin, VIP, glucagon, bombesin, CCK, somatostatin, calcitonin gene-related peptide, and the like.

The genetically modified NS4 cells can be implanted for cell therapy or gene therapy into the CNS of a recipient in need of the biologially active molecule produced by the genetically modified cells. Transplantation techniques are detailed below.

Alternatively, the genetically modified NS4 cell can be subjected to various differentiation protocols in vitro prior to implantation. For example, genetically modified NS4 cells may be removed from the culture medium, which allows proliferation and differentiated using any of the protocols, described above. The protocol used depends upon the type of genetically modified cell desired. Once the cells have differentiated, they are again assayed for expression of the desired protein. Cells having the desired phenotype can be isolated and implanted into recipients in need of the protein or biologically active molecule that is expressed by the genetically modified cell.

Methods for screening effects of drugs on NS4 cells. NS4 cell cultures can be used for the screening of potential neurologically therapeutic compositions. These test compositions can be applied to cells in culture at varying dosages, and the response of the cells monitored for various time periods. Physical characteristics of the cells can be analyzed by observing cell and neurite growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Alternatively, NS4 cells treated with these pharmaceutical compositions can be transplanted into an animal, and their survival, their ability to form neural connections, and their biochemical and immunological characteristics examined.

NS4 cells can be used in methods of determining the effect of a biological agents on neural cells. The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are referred to herein as "neurological agents", a term which encompasses any biologically or pharmaceutically active substance that may prove potentially useful for the proliferation, differentiation or functioning of CNS cells or treatment of neurological disease or disorder. For example, the term may encompass certain neurotransmitters, neurotransmitter receptors, growth factors, growth factor receptors, and the like, as well as enzymes used in the synthesis of these agents.

The biological agent can be the biological agent is selected from the group consisting of basic fibroblast growth factor, acid fibroblast growth factor, epidermal growth factor, transforming growth factor α, transforming growth factor β, nerve growth factor, insulin like growth factor, platelet derived growth factor, glia-derived neurotrophic factor, brain derived neurotrophic factor, ciliary neurotrophic factor, phorbol 12-myristate 13-acetate, tryophotin, activin, thyrotropin releasing hormone, interleukins, bone morphogenic protein, macrophage inflammatory proteins, heparan sulfate, amphiregulin, retinoic acid, tumor necrosis factor α, fibroblast growth factor receptor, epidermal growth factor receptor. Examples of biological agents include trophic factors such as glial-derived neurotrophic factor (GDNF); regulators of intracellular pathways associated with growth factor activity such as staurosporine, CGP-4 1251, and the like; hormones; various proteins and polypeptides such as interleukins and the Bcl-2 gene product; oligonucleotides such as antisense strands directed, for example, against transcripts for receptors; heparin-like molecules; and a variety of other molecules that have an effect on radial glial cells or CNS neural stem cell.

To determine the effect of a potential biological agent on neural cells from a particular host, a culture of NS4 cells can be obtained from normal neural tissue or, alternatively, from a host afflicted with a CNS disease or disorder. The choice of culture conditions depends upon the particular agent being tested and the effects one wants to achieve. Once the cells are obtained from the desired donor tissue, they are proliferated in vitro in the presence of a proliferation-inducing growth factor.

The ability of various biological agents to increase, decrease or modify in some other way the number and nature of the NS4 cells can be screened on cells proliferated in the presence of EGF or other proliferation-inducing factor by the methods described in EXAMPLE 1-2.

It is possible to screen for biological agents that increase the proliferative ability of NS4 cells which would be useful for generating large numbers of cells for transplantation purposes. It is also possible to screen for biological agents that inhibit NS4 cell proliferation. NS4 cells are plated in the presence of the biological factors of interest and assayed for the degree of proliferation that occurs. The effects of a biological agent or combination of biological agents on the differentiation and survival of NS4 cells and their progeny can be determined.

It is possible to screen NS4 cells which have already been induced to differentiate prior to the screening. It is also possible to determine the effects of the biological agents on the differentiation process by applying them to NS4 cells prior to differentiation. Generally, the biological agent can be solubilized and added to the culture medium at varying concentrations to determine the effect of the agent at each dose. The culture medium may be replenished with the biological agent every couple of days in amounts so as to keep the concentration of the agent somewhat constant.

Changes in proliferation are observed by an increase or decrease in the number of neurospheres that form or an increase or decrease in the size of the neurospheres (which is a reflection of the rate of proliferation as determined by the numbers of NS4 cells per neurosphere). A "regulatory factor" is a biological factor that has a regulatory effect on the proliferation of NS4 cells. For example, a biological factor would be considered a "regulatory factor" if it increases or decreases the number of NS4 cells that proliferate in vitro in response to a proliferation-inducing growth factor (such as EGF). Alternatively, the number of NS4 cells that respond to proliferation-inducing factors may remain the same, but addition of the regulatory factor affects the rate at which the NS4 cells proliferate. A proliferation-inducing growth factor may act as a regulatory factor when used in combination with another proliferation-inducing growth factor.

Other regulatory factors include heparan sulfate, TGF, activin, BMP-2, CNTF, retinoic acid, TNF, MIP-1, MJP-2, NGF, PDGF, interleukins, and the Bcl-2 gene product. Other factors having a regulatory effect on stem cell proliferation include those that interfere with the activation of the c-fos pathway (an intermediate early gene, known to be activated by EGF), including phorbol 12 myristate 13-acetate (PMA; Sigma), which up-regulates the c-fos pathway and staurosporine (Research Biochemical International) and CGP-41251 (Ciba-Geigy), which down regulate c-fos expression and factors, such as tyrphostin (Fallon et al., 11(5) Mol. Cell Biol. 2697-2703 (1991)) and the like, which suppress tyrosine kinase activation induced by the binding of EGF to its receptor.

The regulatory factors are added to the culture medium at a concentration in the range of about 10 pg/ml to 500 ng/ml (preferably, for example, about 1 ng/ml to 100 ng/ml, or more preferably about 10 ng/ml). The regulatory factor retinoic acid is prepared from a 1 mM stock solution and used at a final concentration between about 0.01 μM and 100 μM (preferably, for example, between about 0.05 μM to 5 μM).

The glycosaminoglycan, heparan sulfate, is a ubiquitous component on the surface of mammalian cells known to affect a variety of cellular processes, and which binds to growth factor molecules such as FGF and amphiregulin, thereby promoting the binding of these molecules to their receptors on the surfaces of cells. Heparan sulfate can be added to the culture medium in combination with other biological factors, at a concentration of about 1 ng/ml to 1 mg/ml (preferably, for example, about 0.2 μg/ml to 20 μg/ml, or more preferably about 2 g/ml).

Using these screening methods, one of skill in the art can screen for potential drug side-effects on pre-natal and post-natal CNS cells by testing for the effects of the biological agents on neural cell proliferation and differentiation or the survival and function of differentiated CNS cells. The proliferated NS4 cells are typically plated at a density of about $5-10\times10^6$ cells/ml. if it is desired to test the effect of the biological agent on a particular differentiated cell type or a given make-up of cells, the ratio of neurons to glial cells obtained after differentiation can be manipulated by separating the different types of cells. Astrocytes can be panned out after a binding procedure using the RAN 2 antibody (available from ATCC). Tetanus toxin (available from Boerhinger Jngelheim) can be used to select out neurons. By varying the trophic factors added to the culture medium used during differentiation it is possible to intentionally alter the phenotype ratios. Such trophic factors include EGF, FGF, BDNF, CNTF, TGF, GDNF, and the like. For example, FGF increases the ratio of neurons, and CNTF increases the ratio of oligodendrocytes. Growing the cultures on beds of glial cells obtained from different CNS regions can also affect the course of differentiation.

The effects of the biological agents are identified based upon significant differences relative to control cultures with respect to criteria such as the ratios of expressed phenotypes (neurons, glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which synthesize these molecules.

The factors involved in the proliferation of NS4 and the proliferation, differentiation and survival of NS4 cell progeny, and their responses to biological agents can be isolated by constructing cDNA libraries from NS4 cells or NS4 cell progeny at different stages of their development using techniques known in the art. The libraries from cells at one developmental stage are compared with those of cells at different stages of development to determine the sequence of gene expression during development and to reveal the effects of various biological agents or to reveal new biological agents that alter gene expression in CNS cells. When the libraries are prepared from dysfunctional tissue, genetic factors may be identified that play a role in the cause of dysfunction by comparing the libraries from the dysfunctional tissue with those from normal tissue. This information can be used in the design of therapies to treat the disorders. Additionally, probes cant be identified for use in the diagnosis of various genetic disorders or for use in identifying neural cells at a particular stage in development.

Electrophysiological analysis can be used to determine the effects of biological agents on neuronal characteristics such as resting membrane potential, evoked potentials, direction and ionic nature of current flow and the dynamics of ion channels. These measurements can be made using any technique known in the art, including extracellular single unit voltage recording, intracellular voltage recording, voltage clamping and patch clamping. Voltage sensitive dyes and ion sensitive electrodes may also be used.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented to more fully illustrate the preferred embodiments of the invention. These EXAMPLES should in no way be construed as limiting the scope of the invention, as defined by the appended claims.

Example 1

Dissociation of Murine Embryonic Neural Tissue and Proliferation of Murine NS4 Cells Separate embryonic (E12-15) primary neural cultures were established by mechanical or enzymatic dissociation from the striatal anlage (lateral ganglionic eminence and medial ganglionic eminence) and grown in DMEM, 10% FCS, N2 supplement and EGF (20 ng/ml) for 4-20 passages. The cells grew adherently and phenotypes were analyzed using morphology and immunocytochemistry. For immunocytochemistry analysis, cells were fixed in 4% paraformaldehyde for 10 min. and exposed to primary and secondary antibodies according to well-established protocols. For neuronal differentiation, cells were switched to serum-free medium without EGF. After 1-7 days, cells were fixed and evaluated by morphology and immunocytochemistry. To evaluate the paternal origin of the differentiated progeny, cultures were established from embryonic transgenic mouse lateral ganglionic eminence and MGE expressing the receptor of the avian RCAS virus (called tv-a) under the control of the GFAP promoter. Thus, only cells that express GFAP can be infected by an RCAS-EGFP vector, which in turn marks the cells with green fluorescence. Therefore, any neuron that is derived from a cell that once expressed GFAP is rendered fluorescent.

After a couple of passages, the parental culture shows >95% GFAP and nestin immunoreactivity. In addition, the cultures express the radial glial marker RC2. After switching to serum-free medium and removing the EGF (differentiating condition), the cells change morphology and staining pattern to become as much as 36% neurons (as determined by morphology and, beta-tubulin III). This finding could be reproduced with cells at least 15 passages old. The fact that the neurons had arisen from GFAP$^+$ parental cells was established beyond doubt by using the transgenic mouse cultures. Many of the, beta-tubulin III immunoreactive cells also expressed EGFP indicating that they had been GFAP$^+$ at an earlier time point. Last, some cells retained their molecular identity and express transcription factors typical of differentiating neurons in the lateral ganglionic eminence (e.g. DLX and MEIS2), showing that the cells are specified progenitors.

Example 2

Dissociation of Human Embryonic Neural Tissue and Proliferation of Human NS4 Cells Human first trimester CNS tissue was collected and the LGE and MGE were dissected out and mechanically dissociated and cultured in DMEM, N2 supplement, 10% FCS ("NS4 Complete Medium"), and EGF (20 ng/ml) or EGE and bFGF (20 ng/ml each). The tissues were incubated in 0.1% trypsin and 0.05% DNase in DMEM for 15-20 min at 37° C. Tissue was mechanically dissociated with a fire polished Pasteur pipette. Dissociated cells were plated at high density in tissue culture treated flasks without additional coating in "NS4 Complete Medium" and either EGF (20 ng/ml) or EGF and bFGF (20 ng/ml each). Cell cultures were housed in an incubator at 37° C., 100% humidity, 95% air/5% $CO_2$. When the cultures were confluent, they were passaged 1:3.

After several passages (>4), parental cells were investigated for their morphology and expression of GFAP, nestin, and, beta-tubulin III. Similar to the mouse cultures (EXAMPLE 1), human cells were placed in serum-free medium without growth factors and the differentiation studied with morphology and immunocytochemistry. Adherent human cell cultures could be established in a similar manner to mouse cultures (EXAMPLE 1).

After several passages, a majority of cells showed GFAP and nestin Inimunoreactivity and glial morphology. Both the EGF and EGF and bFGF stimulated cultures appeared similar in morphology and immunoreactive pattern. Upon switching to SFM and removal of growth factors, cells convened into a neuronal morphology in similar or possible even larger numbers than the mouse cultures and became immunoreactive to the neuronal marker, beta-tubulin III.

Example 3

Glial Methods

Lateral ganglionic eminence and medial ganglionic eminence sections were dissected from E13.5 or E15.5 embryos. The tissue pieces were incubated in 0.1% trypsin and 0.05% DNase in DMEM for 15-20 min at 37° C. before mechanical dissociation and plating, at high density in tissue culture treated flasks without additional coating. Cells were expanded in DMEM F12 with N2 supplement (Gibco), glutamine (2 mM), antibiotics, 10% fetal calf serum (FCS), and EGF (20 ng/ml). When the cultures were confluent, they were passaged 1:3. Both neurons and glia were present in the initial cultures. However, by the 4th passage (P4), or after freezing and thawing, the cultures were devoid of cells possessing neuronal morphologies or expressing neuronal markers (i.e., beta-tubulin III). These cultures were highly enriched in cells expressing nestin as well as glial phenotypes (i.e. GFAP and RC2). In the case of LGE glial cultures, the cells were expanded extensively (passaged>25 times). These cultures expressed similar phenotypes to those passaged fewer times.

To generate neurones a medium-switch was performed on confluent cultures (3 days after plating and splitting) from the expansion medium to the same medium minus the serum and EGF. In some cases, a sequential switch was performed, where first serum was removed and then EGF a few days later. These cultures were kept in the serum-free medium (without EGF) for 4-8 days before fixation in 4% PFA and immunostaining for neuronal and glial markers (e.g., beta-tubulin III, GFAP, nestin and RC2).

Example 4

Longterm EGF-Stimulated Cultures of Attached $GFAP^+$ Cell

In this EXAMPLE, cultures of dissociated cells prepared from lateral ganglionic eminence of the mouse embryonic day 15-17 (E15-17) forebrain were established in a medium including epidermal growth factor (EGF) and serum, to obtain propagating attached cultures with a high content of astroglia-like cells. This EXAMPLE is to determine the long-term characteristics of cells cultured under these conditions. The cultures were passaged at confluency, and growth rate, morphology and phenotypic properties (e.g. GFAP immunoreactivity) were assessed after the subsequent passages. The cultured cells had the morphology of astroglial cells, with the vast majority of the cells immunoreactive for GFAP (around 90%), as well as for the intermediate filament marker nestin. The cells were also positive for the mouse-specific neural antibodies M2 and M6. The cells were negative when stained for the neuronal marker, beta-tubulin III.

Dissociation. Lateral ganglionic eminence tissue was retrieved mainly from E15, but in a few cases also from E16-17, mouse embryos of timed pregnant mice. With the embryos immediately placed in a 1:1 mixture of Dulbecco's minimum essential medium (DMEM) and F12 (Gibco), the brains were removed, the cortex unfolded after a medial parasagittal cut and the underlying lateral ganglionic eminence dissected out bilaterally, using the method of Olsson et al., 69 Neuroscience 1169-82 (1995). The tissue pieces, collected from one litter of embryos at a time, were then placed in a 0.1% trypsin (Worthington Biochemical Corporation)/ 0.05% DNase (Sigma) solution in DMEM/F12 and incubated for 20 mm at 37° C. Following rinses in DMEM/F12 with 0.05% DNase, the pieces were mechanically dissociated by repeated gentle trituration through the tips of two Eppendorf pipettes with decreasing diameters and centrifuged for 5 mm at 600 rpm. The pellet was then resuspended and plated onto uncoated T75 flasks (Falcon), with a medium containing DMEM/F12 supplemented with 10% Fetal Bovine Serum (FBS; Sigma), EGF (20 ng/ml, human recombinant; R & D Systems), a defined hormone and salt mixture including 20 µg/ml insulin, 100 µg/ml transferrin, 20 µM progesterone, 60 µM putresciene and 30 nM sodium selenite (all from Sigma Chemicals, St. Louis Colo.; see, Weiss et al., 16 J. Neurosci. 7599-609 (1996)) and 1% AAS (antibiotic antimycotic solution; Sigma). The cultures were maintained at 37° C. with 95% air and 5% $CO_2$, with the medium changed every 2-3 days, and the cells passaged (or frozen down using DMSO and serum) at confluency.

In vitro cell cultures. The cultures were passaged at confluency, and growth rate, morphology and phenotypic properties (e.g. GFAP immunoreactivity) were assessed after the subsequent passages. After an initial in vitro study, with the cells evaluated over five passages ("In vitro A"), a second more extensive in vitro characterization ("In vitro B") was initiated. To address the importance of the EGF, control cultures without the trophic factor were studied both during the initial culture period, and at later passages.

In the initial in vitro cultures ("In vitro A"), E15-17 LGE-cells from three litters were dissociated, split and plated into six T75s, and subsequently split 1:5 at confluency into T75s (n=6), with assessment of growth rate and proportion of GFAP-immunoreactive over the first five passages.

In the second more extensive and long-term cultures ("In vitro B"), LGE tissue was obtained from three E15 litters, with plating into two T75 flasks for each litter. Thus, six different cultures were followed over the subsequent passages. When the cells reached confluency, a defined number of $1.7 \times 10^6$ cells were plated onto each new T75.

After each of the passages, the cell doubling time ($t_2$) and days needed to reach confluency were assessed and the mean values for the six different cultures plotted as functions of the passage number. $t_2$ was defined as the natural logarithm of 2 divided by the k-value (1n2/k) of a growth curve showing the change in cell number (logarithmized) as a function of time. The growth curve was determined by placing a counting grid at six randomly marked positions at the bottom of each flask, and calculating the average cell number in the grid area for each flask (n=6) and time-point. Initially, the growth curves were based on cell counts made 1-2 times per day, as compared to only 2-3 times a week during the more slowly proliferating stages.

Figure 5:
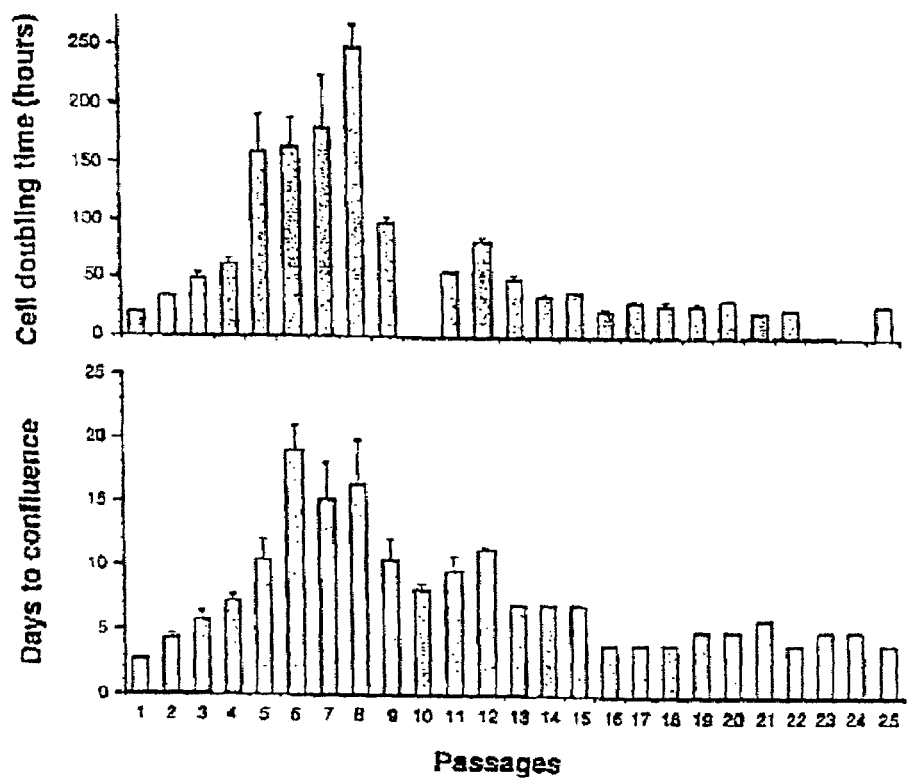
FIG. 5 are histograms that describe the growth characteristics over the repeated passages, expressed as "Cell doubling time" (hrs) and "Days to confluency", after each passage. The cells showed a high growth activity during the initial four passages, but with a significant decrease in growth rate during passages 6-8, after which the rate of division increased again to values similar to those during the initial culture period and then remained stable throughout the test, i.e. at least until passage 25 (seven months).

As shown in FIG. 5, which presents data from the second more extensive culture cultures ("In vitro B"), measurements of "Days to confluency" and "Cell doubling time" revealed a high mitotic activity in the cultures after each of the first four passages, but with a gradual decrease in growth rate, which continued and became more significant after passages 6-8. The mean of the "Cell doubling time" during passages 5-8 was significantly higher than during the initial four passages (paired Student t test, $p<0.01$). The same growth pattern was also observed in the first set of cultures ("In vitro A"), although then only quantified over the first five passages (data not shown), but when the cultures were left to grow further for several months, it was found that after a period of slow growth, the cells started to divide more readily again. Similarly, in the second set of cultures ("In vitro B"), the rate of division increased again after passage nine and thereafter stabilized at values equal to the initial culture period (FIG. 5.

Observations of in vitro cell cultures. From a few days after the dissection and initial plating, the cultures grew well, with smaller phase-bright cells and clusters of tightly aggregated cells, resembling so-called "neurospheres" (Reynolds & Weiss, 175 Dev. Biol. 1-13 (1996)), situated on top of dense islands of attached cells. Already after passage two, the cultures were more homogeneous, with small and tight islands of elongated attached cells, with short arm-like processes. Over the first few passages, the majority of the cells gradually became more flat and epitheloid, with a cubical or polygonal shape, and with fewer processes and more round and distinct nuclei, and thus resembling type I astroglial cells. During the slowly dividing passages (passages 5-8) the morphology of the cells changed, to a larger and more flat and round appearance, with long and thin processes and with cells less densely aggregated on the bottom of the flask. After passage 8 the cells reassumed the morphology of the early passages.

In control cultures from passage 11 without EGF, cells attached well after plating, but ceased to proliferate further, as followed over five weeks. The cell morphology also changed into a larger and more flat appearance, with long and thin processes extending from the cell body. Separate cultures were also prepared, without EGF already from the first plating and start of the cultures, and here no or very little growth was observed during the subsequent six weeks. These cells had a morphology resembling that of the passage 11 control cultures after EGF removal.

Figure 4:
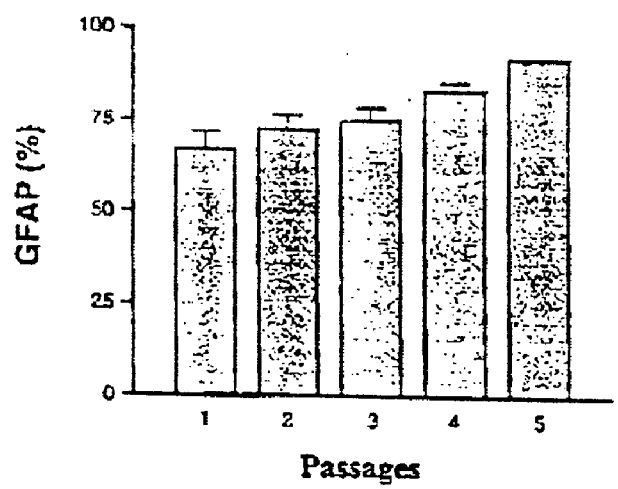
FIG. 4 is a histogram illustrating the astroglial phenotype of the attached cells in vitro, as assessed by GFAP-immunocytochemistry after each passage, until passage five, when approximately 90% of the cells were GFAP$^+$.

Immunoreactivily. GFAP-immunocytochemistry, performed after each of the first five passages and after passage 18, revealed that around 75% of the cells were $GFAP^+$ already after passage two, and with approximately 90% $GFAP^+$-immunoreactive cells after passage five, and also after passage 18 (FIG. 4). A similar proportions of the cells also expressed the intermediate filament nestin, both at the early and late passages. The mouse-specific neural markers M2 and M6 were also detected in the majority of the cells, overlapping with the GFAP and nestin immunoreactivities, but with a reduced expression of M2 at the later passages, and with M6 in general expressed at lower levels than M2. No or only occasionally, beta-tubulin $III^+$ cells were detected at either passage five or 18. For immunocytochemistry, 100,000 cells were plated in uncoated 4-well plates (NUNC) after each passage, and after attachment fixed in 4% paraformaldehyde (PFA). After rinses with potassium phosphate buffered saline (KPBS), the cultures were preincubated with 5% normal serum raised in the same species as the secondary antibody, in 0.02 M KPBS for 1 hr at room temperature (RT). Following incubation with primary antibodies (overnight at 4° C.), the cultures were rinsed three times in 0.02 M KPBS (with 5% serum), and incubated with a biotinylated secondary antibody (2 hrs, 1(T), rinsed in KPBS and incubated with an avidin-biotin-peroxidase complex (Vectastain-Elite ABC Kit PK-6 100) using 3,3-diaminobenzidine as chromogen (25 mg/ml; Sigma).

Analysis of long-term attached cultures of $GFAP^+$ $nestin^+$ cells. We observed poor plating and growth in the control cultures initiated without EGF. We also observed a shift in growth rate during the extensive culture period, with about 25 passages over 7 months. The initially high rate of cell division gradually decreased over the first 8 passages, after which the cells increased their growth rate again, stabilizing at values equal to the first 4 passages, thus with features of a cell line (FIG. 5).

Figure 3:
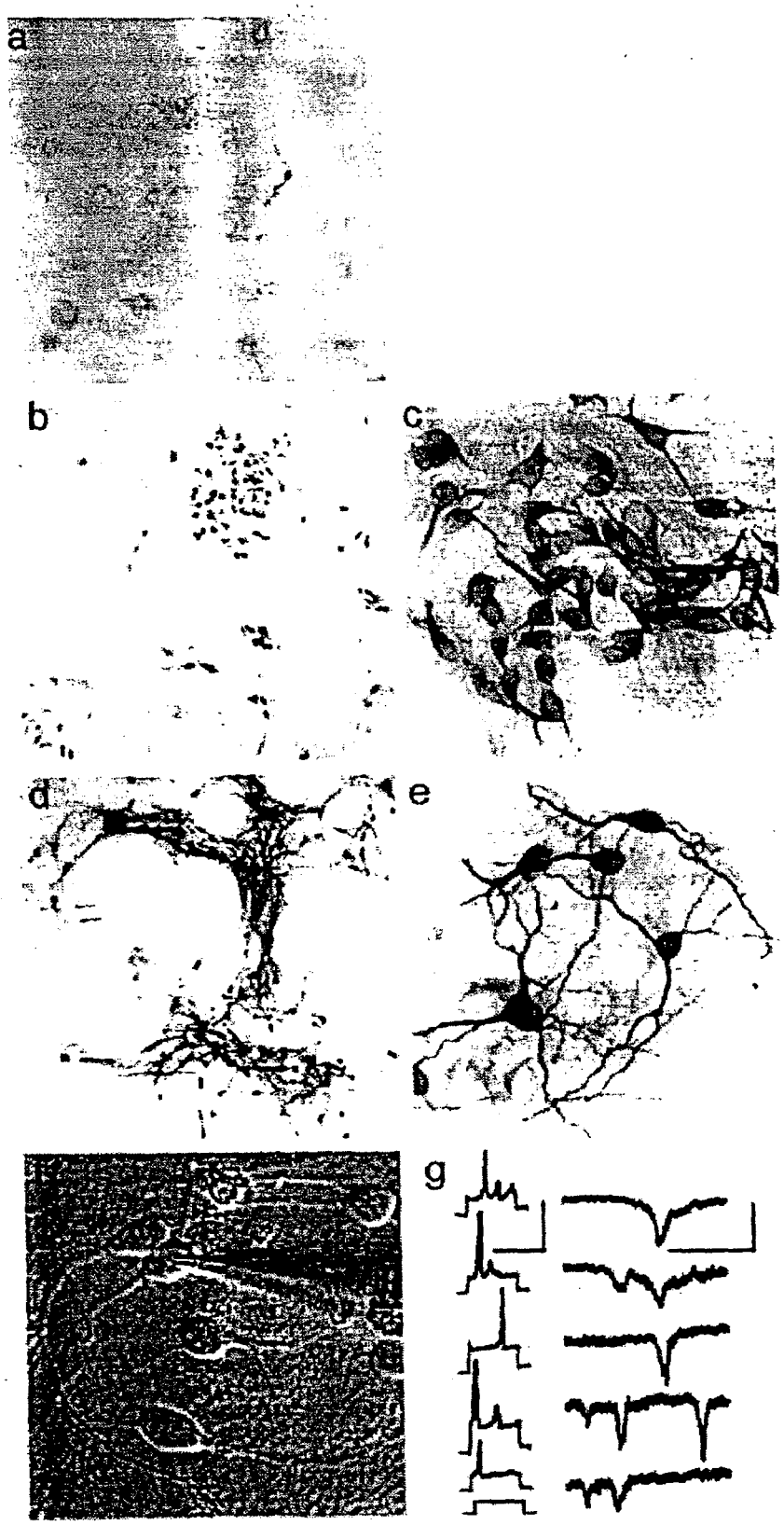
FIG. 3 illustrates the generation of neurons from LGE glia. (a) Beta-III-tubulin positive cells were severely deficient in the glial cultures grown in the expansion medium (i.e. containing serum and EGF). Note the lone cell exhibiting a neuronal morphology. (b and c) Three days after removal of both serum and EGF, numerous beta-III-tubulin-positive cells with neuronal morphology were present. (d and e) Cultures maintained for 7 days without EGF and serum; contained beta-III-tubulin-positive cells displaying distinctive neuronal morphologies. (f) High power of an in vitro generated neuron with the patch-clamp pipette attached. (g) Spike-like activity induced by step depolarization (traces on the right; vertical scale, 100 mV; horizontal scale, 500 ms) and spontaneous inward currents (traces on the left; vertical scale 100 pA; horizontal scale, 500 ms) in 5 different cells.

The early and late passage cells have many similarities in addition to the morphological and immunocytochemical characteristics presented here, such as immunoreactivity also for the radial glia marker RC-2 (FIG. 3).

Example 5

Differentiation of NS4 Cells into Neurons and Glia

To generate neurons, cells were proliferated as in EXAMPLES 1 or 2 on uncoated tissue culture plastic. Three days after plating, a medium switch was performed from the expansion medium to the same medium minus the serum and EGF. In some cases, a sequential switch was performed, where first serum was removed and then EGF a few days later. Cultures for indirect immunocytochemistry, were kept in the serum-free medium (without EGF) for 4-8 days before fixation in 4% paraformaldehyde in PBS. Following a 10 mm fixation, coverslips were washed three times in PBS and immunostained for neuronal and glial markers (e.g. beta-tubulin III, GFAP, nestin, and RC2). Coverslips were incubated with primary antiserum in PBS/10% normal goat serum, 0.3% TRITON-X-100 for two hours at 37° C. Coverslips were washed 3× in PBS and incubated with labeled secondary antibodies for 30 mm at 37° C. Coverslips were then washed 3× in PBS, rinsed with water and placed on glass slides. Between 17-36% of the cells derived from cell cultures established from different dissections including human LGE, were neurons as determined by morphology and beta-tubulin III staining. To further examine the neuronal differentiation, ICC staining for GABA and calbindin were done indicating that most of the cells formed a GABA-ergic neuronal phenotype. Furthermore, the cells showed other evidence of retention of the striatal specification such as the expression of the marker DLX1 and MEIS2 but not PAX6 and NKX2.1, markers of cortical and MGE neurons respectively. The neuronal phenotype and function was further confirmed by electrophysiology which demonstrated electrochemical activity characteristic of neurons. During differentiation, many cells co-labeled with both beta-tubulin III and GFAP. With further differentiation mature neuronal and astrocytic phenotypes and separate beta-tubulin III and GFAP immunoreactivity were observed.

Example 6

Generation of Neurons from Multipassage Glial Cultures and Confirmation of Glial Origin Embryonic glial cells can be grown and expanded for several months in EGF and serum-containing medium, with a majority of the cells expressing high levels of GFAP and nestin, even after 25 passages. In this EXAMPLE, we used such glial cultures derived from the mouse telencephalon (E13.5 and E15.5); the LGE (lateral ganglionic eminence) and the MGE (medial ganglionic eminence). We show that after 4 to 25 passages, high numbers of neurons can be generated from these cells simply by removing serum and EGF from their culture medium.

The neurons we generate turn on, not only the neuron-specific marker, beta-tubulin III, but also MEIS2 and DLX, transcription factors specific for the regions where the glia were dissected from.

To determine whether the neurons actually derive from glial cells we used cell cultures from the GFAP-tva mouse. These mice express the receptor for the RCAS-virus, tva, under the GFAP promoter (see, EXAMPLE 1). Thus, only GFAP expressing cells can be infected. After infection with an RCAS(A)GFP (green fluorescent protein) virus, GFP cells were found that were also, beta-tubulin III$^+$ and had a neuronal morphology. These results show that a subpopulation of GFAP$^+$ cells in multipassage glial cultures derived from the ventral telencephalon are indeed neuronal precursors.

Example 7

Transplantation of NS4 Cells into Adult and Neonatal Rats

After passages 4 to 6 and passage 18 of the cells in EXAMPLE 3, in vivo studies were conducted to analyze the survival, morphology and migratory patterns of the cultured cells after transplantation. Thus, cell suspensions were prepared from the cultures, and implanted cross-species into the striatum of immunosuppressed intact or lesioned adult rats, and into neonatal rats. At 4 weeks post-transplantation, the grafts were analyzed through immunohistochemistry and in situ hybridization, using species-specific and phenotypic markers.

Method of transplantation into adults. Twelve adult female Sprague-Dawley rats (BK Universal, Sweden) were the adult graft recipients. For surgery, the rats were anaesthetized with Equithesin (0.3 ml/100 g body weight) and placed in a Kopf stereotaxic frame. A total of 1.4 l ibotenic acid (10 g/l dissolved in 0.1 M phosphate buffer (PB; Sigma) were injected into the head of the right caudate-putamen, divided over three sites:
 (1) A=+0.2; L=−3.0; V=−5.5 (0.5 l);
 (2) A=+0.2; L=−3.0; V=−4.0 (0.5 ll);
 (3) A=+1.5; L=−2.5; V=−4.7 (0.4 pl)
(tooth bar at 2.3; the ventral (V) coordinate was measured from the dural surface; A, anterior and L, lateral to bregma).

One to two weeks after the lesion, suspensions with cells from passages 4-5 cultures were implanted into the ibotenic acid-lesioned area and into the contralateral intact striatum of the adult recipient rats. To prepare the cell suspensions, the culture medium was replaced by Hank's Balanced Salt Solution without magnesium and calcium (HBSS; GIECO), for 1 min and after an incubation with 0.1% trypsin solution for 4 mm at 37° C., serum-containing medium was added and the cells were detached from the flasks. After centrifugation for 5 mm at 600 rpm, the cells were resuspended in HBSS (with magnesium and calcium), counted in a hemocytometer, and prepared into a single cell suspension with a cell density of 50,000 cells/l. The suspensions were injected from a Hamilton syringe with a total of 2 or 4 pl implanted into each striatum at the following coordinates:
 (1) A=+0.4; L=+/−2.8; V=(a)−5.0, (b)−4.5;
 (2) A=+0.8; L=+/−2.5; V=(a)−5.0, (b)−4.5
 (tooth bar at 2.3).

The adult host rats were immunosuppressed by daily intraperitoneal (ip) injections of cyclosporin A (10 mg/mm; 1 ml/kg body wt), from one day before transplantation until sacrifice.

Method of transplantation into neonates. Cell suspensions from passages 4-6 ("Neonate a") and passage 18 ("Neonate b") cultures (from EXAMPLE 4) were injected into the striatum bilaterally in 27 neonatal rats and unilaterally into five neonates, with a cell density adjusted to 25 000 cells/pl or 100,000 cells/pl. The injections were made from glass capillaries attached to a Hamilton syringe and in all cases the neonates were placed in a neonatal frame during surgery (see, Cunningham & McKay, 47 J. Neurosci. Methods 105-14 (1993)). In total, 2 l/neonatal striatum were injected at the following coordinates:
 (1) A+0.5; L+/−2.2; V(a)−3.0, (b)−2.5;
 (2) A +0.9; L+/−1.9; V(a)−3.0, (b)−2.5;
 with bregma and lambda at the same horizontal level.

Immunohistochemistry after transplantation. Four weeks after transplantation, the rats were anaesthetized with an overdose of pentobarbital (ip) and transcardially perfused with 200-300 ml ice-cold 4% PFA in 0.1 M phosphate buffer (PB). The brains were removed, postfixed for 6 hrs in the same fixative and then soaked overnight in 0.1 M PB containing 25% sucrose. The brains were sectioned in the coronal or sagittal planes at 30 m, using a sliding knife freezing microtome (Leica SM 20001). Endogenous peroxidase activity was quenched with 3% $H_2O_2$ in KPBS (10 min). The sections were reacted as described above for the in vitro immunocytochemistry, using either biotinylated, or Cy2-conjugated or Cy3-conjugated secondary antibodies. The sections were then mounted onto chrome-alum coated slides, dehydrated and coverslipped with DPX (BDH). The sections incubated with a Cy2-conjugated or Cy3-conjugated secondary antibody were directly mounted and coverslipped with PVA/DABCO.

In selected sections, double immunohistochemistry was performed to simultaneously visualize both M2 and M6 or both M2 and GFAP. For the M6 and M2, double staining was performed. The M6 epitope was first labeled with the M6 antiserum and a secondary Cy3-conjugated anti-rat antibody, followed by M2-staining with a primary biotinylated M2-antiserum and an avidin-Cy2-complex. For the different protocols, controls with omission of primary antibodies were negative.

In situ hybridization. Sections were processed for in situ hybridization to detect mouse satellite DNA. After additional fixation for 10 min in 4% PFA, the sections were first incubated in 2×SSC and 5 mM EDTA at 37° C., and then digested with protease from *Streptomyceus griseus* (25 g/ml; Sigma) in 2×SSC and 5 mM EDTA (pH 8.0) for 10 min at 37° C. Then followed dehydration in ascending ethanols, and denaturation in 70% formamide (2×SSC) for 10 min at 90° C. After additional dehydration with ice-cold ethanols, hybridization was carried out overnight at 37° C. with a digoxigenin end-labeled oligonucleotide probe to mouse satellite DNA, in 65% formamide, 2×SSC, 250 g salmon sperm DNA. After washes, the hybridized probe was visualized using a fluorescein-labeled antibody to digoxigenin (Boehringer Ingelheim). After in situ hybridization, the sections were additionally stained with antibodies against either GFAP or NeuN, using the same protocol as described above, although performed on these already mounted sections, and with a Cy3-labeled secondary antiserum.

In vivo/transplantation studies. TABLE 1 summarizes the outcome of the transplantations, with cells from passages 5-6 implanted into adult intact and lesioned striatum, and cells from either passages 4-6 or passage 18 injected into the neonatal striatum ("Neonate a" and "Neonate b", respectively).

TABLE 1

Summary of the grafts implanted into the striatum of intact or lesioned adult rats, and of neonatal rats. The neonatal rats received cells from either passages 4-6 ("Neonate a") or passage 18 ("Neonate b"), and the adult animals from passage 5-6. Note the differences in the amounts of cells transplanted per striatum.

| Transplant group | Treatment | Donor cells (Passage) | Number of cells/ striatum | Number of transplants | Number of positive transplants |
|---|---|---|---|---|---|
| Adult | Lesion | 5 | 200,000 | 7 | 4 |
| | Intact | 5 | 200,000 | 7 | 5 |
| | Lesion | 4 | 100,000 | 5 | 5 |
| | Intact | 4 | 100,000 | 5 | 5 |
| Total | | | | 24 | 19 |
| "Neonate a" | Intact | 6 | 100,000 | 14 | 5 |
| | Intact | 6 | 200,000 | 5 | 1 |
| | Intact | 4 | 100,000 | 14 | 10 |
| | Intact | 6 | 50,000 | 10 | 5 |
| Total | | | | 43 | 21 |
| "Neonate b" | Intact | 18 | 100,000 | 16 | 11 |
| Total | | | | 16 | 11 |

In the adult transplanted animals, surviving cells were found in 9 out of 11 lesioned and 10 out of 12 intact striata (TABLE 1). As shown in TABLE 2, the M2$^+$ cells were primarily located along the needle tract, densely aggregated in a graft core and with only a restricted migration into the surrounding striatum, both after implantation into the intact and into the lesioned side. The graft core was significantly larger in the specimens receiving 200,000 as compared to 100,000 cells ($F(1.15)=6.7$, $p<0.05$, two-way ANOVA), but not significantly different between the lesioned and intact sides, although there was a trend towards larger grafts and graft cores on the lesioned sides (TABLE 2). Migration of M2$^+$ cells occurred for up to 0.6 mm away from the needle tract, with no significant effect of either the implantation site (intact vs. lesion) or number of implanted cells (TABLE 2). Cells in the periphery of the core, and cells that had migrated for some distance, presented an astroglia-like morphology with many short processes.

TABLE 2

Summary of the adult recipients which contained M2-immunoreactive grafts, with measurements of the diameter of the graft core (m), the maximal cell migration distance (m) (intact and lesioned side respectively) and with the mean numbers for each of the groups with different numbers of implanted cells. The graft core was defined as the region of dense M2-immunoreactivity around the needle tract and the maximal cellmigration distance was measured from the visible needle tract.

| Animal No. | Number of transplanted cells/striatum | Intact side Diameter of graft core (Om) | Intact side Maximal cell migration (Om) | Lesioned side Diameter of graft core (Om) | Lesioned side Maximal cell migration (Om) |
|---|---|---|---|---|---|
| 1 | 200,000 | 350 | 210 | 950 | 710 |
| 2 | | 850 | 500 | 800 | 650 |
| 3 | | 260 | 950 | — | — |
| 4 | | 400 | 1050 | 400 | 300 |
| 5 | | 400 | 500 | 460 | 350 |
| Mean | | 452 | 642 | 652.5 | 502.5 |
| 6 | 100,000 | 350 | 250 | 400 | 550 |
| 7 | | 250 | 500 | 550 | 500 |
| 8 | | 120 | 500 | 200 | 100 |
| 9 | | 250 | 500 | 300 | 340 |
| 10 | | 200 | 600 | 600 | 400 |
| Mean | | 234 | 470 | 410 | 378 |

When grafting cells from passages 4-6 into neonates ("Neonate a"), M2$^+$ grafts were found in 21 out of 43 grafted striata (TABLE 1), with no marked differences in graft survival or migration patterns due to differences in the numbers of implanted cells (TABLE 3). The transplanted cells migrated all over the striatum, along the internal capsule and in large numbers into the globus pallidus, with smaller numbers of cells distributed also in other adjacent areas (TABLE 3). The M2$^+$ cells were small and bush-like with numerous short processes and appeared morphologically similar to mature gray matter (type I) astrocytes.

With grafts of passage 18 (i.e. six month-old) cultures, M2$^+$ cells were found in 11 out of 16 grafted striata (TABLE 1). As shown in TABLE 3, these implants were similar to the early passage grafts, both in cellular morphology and migration patterns, although with an overall reduction in the total number of M2$^+$ cells.

TABLE 3

Summaries of the neonatal recipients containing M2-immunoreactive grafts after implantation of cells from (a) passages 4-6 ("Neonate a") or (b) passage 18 ("Neonate b"). The TABLE shows the numbers of cells transplanted per striatum, the distribution and a relative rating of the numbers of M2$^+$ cells integrated into different regions of the recipient brain (+++, high numbers; ++, moderate numbers; +, low numbers; − no cells detected), cc. corpus callosum; cx, cortex; EP, entopeduncular nucleus; Fr; frontal cortex; hpc, hippocampus; ic, interna capsula; s, septum; Sfi, septofimbrial nucleus; sin, stria medullaris thalamus; Th, Thalamus, VP, Ventral Pallidum.

| Animal no. | | Number of transplanted cells/striatum | Striatum | Globus Pallidus | Single cells in other areas |
|---|---|---|---|---|---|
| "Neonate a" (cells from passages 4-6). | | | | | |
| 1 | Right | 100,000 | +++++ | + | Cx, cc |
| | Left | 100,000 | ++++ | + | — |
| 2 | Right | 100,000 | − | − | — |
| | Left | 100,000 | ++ | + | — |
| 3 | Right | 100,000 | +++ | +++++ | Cc, cx, ic, septum, Sfi |
| | Left | 100,000 | +++ | +++++ | cc, hpc, septum, Sfi |

TABLE 3-continued

Summaries of the neonatal recipients containing M2-immunoreactive grafts after implantation of cells from (a) passages 4-6 ("Neonate a") or (b) passage 18 ("Neonate b"). The TABLE shows the numbers of cells transplanted per striatum, the distribution and a relative rating of the numbers of M2+ cells integrated into different regions of the recipient brain (+++, high numbers; ++, moderate numbers; +, low numbers; − no cells detected), cc. corpus callosum; cx, cortex; EP, entopeduncular nucleus; Fr; frontal cortex; hpc, hippocampus; ic, interna capsula; s, septum; Sfi, septofimbrial nucleus; sin, stria medullaris thalamus; Th, Thalamus, VP, Ventral Pallidum.

| Animal no. | | Number of transplanted cells/striatum | Striatum | Globus Pallidus | Single cells in other areas |
|---|---|---|---|---|---|
| 4 | Right | 200,000 | ++++ | +++ | c, cx, ic, septum |
| 5 | Right | 100,000 | ++++ | ++++ | Septum, Sfi |
|   | Left | 100,000 | ++++ | ++++ | septum, Th |
| 6 | Right | 100,000 | +++++ | ++++ | Cx, EP, hpc, ic, SFi, Th |
|   | Left | 100,000 | +++++ | +++++ | hpc, ic, SFi, VP |
| 7 | Right | 100,000 | ++ | ++ | — |
|   | Left | 100,000 | +++ | ++ | — |
| 8 | Right | 100,000 | ++++ | ++ | ic, |
|   | Left | 100,000 | ++++ | +++ | cx, ic |
| 9 | Right | 100,000 | +++ | +++ | Cc, hpc, ic, SFi, hpc |
|   | Left | 100,000 | +++ | ++ | hpc, ix, SFi, sm |
| 10 | Right | 50,000 | − | ++ | Cc, ic |
|    | Left | 50,000 | − | ++ | ic |
| 11 | Right | 50,000 | ++ | + | Cc, ic |
|    | Left | 50,000 | ++ | ++ | cc, Fr |
| 12 | Right | 50,000 | + | ++ | Cc, cx |
|    | Left | 50,000 | − | — | — |
| "Neonate b" (cells from passages 18). | | | | | |
| 1 | Right | 100,000 | +++ | ++++ | Cc |
|   | Left | 100,000 | +++++ | +++++ | Ic |
| 2 | Right | 100,000 | ++ | ++++ | Ic |
|   | Left | 100,000 | + | +++ | ic, hpc, VP |
| 3 | Right | 100,000 | +++ | ++ | Ic |
|   | Left | 100,000 | ++++ | +++ | — |
| 4 | Right | 100,000 | ++ | +++ | ic, |
|   | Left | 100,000 | ++ | ++ | ic, hpc, Th |
| 5 | Right | 100,000 | +++ | + | Hpc |
|   | Left | 100,000 | ++++ | + | Ic |
| 6 | Right | 100,000 | ++ | − | — |
|   | Left | 100,000 | − | − | — |

In both the neonatal and adult recipients, the majority of the M2+ cells were also M6-immunoreactive. There were, however, no axon-like projections emanating from the regions of M2+/M6+ cells. Using DNA in situ hybridization with a probe recognizing mouse, but not rat, satellite DNA (Br,stle et al., 15 Neuron 1275-85 (1995)), it was possible to confirm the distribution of the M2+ cells within both adult and neonatal recipients. The concentration of cells in the globus pallidus, as revealed by M2-staining, was evident also with the satellite DNA-method. Simultaneous double staining for mouse satellite DNA and with GFAP immunohistochemistry, revealed that in the globus pallidus around 75% of the mouse satellite DNA+ cells were also found to be GFAP-immunoreactive. In the striatum, the overall GFAP-immunoreactivity was lower, with only around 37% of the satellite DNA-labeled cells clearly GFAP+. Using a similar double labeling protocol, only occasional single mouse satellite-stained cells (0.5%) were also, immunopositive for the neuronal antigen NeuN, either in the striatum or in the globus pallidus.

Discussion. Immunohistochemistry for M2 showed that the implanted cells developed an astroglia type I-like morphology, with a distribution overlapping that obtained by mouse-satellite DNA in situ hybridization (Bristle et al., 15 Neuron 1275-85 (1995)). Astroglia-like M2+cells were also positive for M6. No axonal projections were found to emanate from the implanted cells, and only occasional mouse-satellite DNA+ cells could be labeled also with the neuronal marker NeuN. Thus, the implanted cells can survive and integrate well, and acquire an astroglial phenotype after implantation, both when grafted into the neonates and into the adult (lesioned and intact) recipient brains.

These findings from the grafts placed into the neonates and from the adult recipients are in agreement with previous work with grafts of primary ganglionic eminence tissue implanted into rat hosts of different developmental stages (Olsson et al., 79 Neuroscience 57-78 (1997)).

The astroglial nature of the implanted cells was further evidenced by the finding that around 75% of the implanted cells (mouse-satellite DNA+) were GFAP+ in the host globus pallidus. In the striatum, the number of double labeled cells was lower, but also the overall GFAP-staining of the host brain was lower in that region. Interestingly, the pattern of GFAP-immunoreactivity in the grafted cells was thus regionally similar to that of the surrounding host brain.

The migration of astroglial cells from primary tissue-grafts is region specific, and thus dependent on from where the tissue is dissected (Gates et al, 84 Neuroscience 10 13-23 (1998)). Questions regarding the regional specificity of astroglial cells, could also be further addressed by growing relatively pure populations of astroglial cells from different CNS regions using the present or a similar culture protocol.

Importantly, no tumors were formed when implanting late passage cells, even though the cells showed a high growth rate in vitro. Although the late passage cells seemed to survive less well than the early passage ones, also the late passage cells had a clear astroglial morphology and showed similar migration patterns when grafted into the neonatal recipients.

The foregoing descriptions have been presented only for the purposes of illustration and, is not intended to limit the invention to the precise form disclosed, but by the claims appended hereto.

We claim:

1. An in vitro cell culture of RC-2+ cells, wherein
   a) one or more cells in the culture have the capacity to differentiate into neurons;
   b) the cell culture divides in a culture medium containing at least one proliferation-inducing growth factor; and
   c) one or more cells in the culture differentiate into neurons upon withdrawal of the proliferation-inducing growth factor.

2. The cell culture of claim 1, wherein the cells are RC2+ nestin+ cells.

3. The cell culture of claim 1, wherein the cells are derived from the central nervous system of a mammal.

4. The cell culture of claim 1, wherein the cell culture differentiates into at least 10% neurons under differentiation-inducing culture conditions.

5. The cell culture of claim 1, wherein, under differentiation-inducing culture conditions, the majority of differentiated neuronal cells have a GABA-ergic phenotype.

6. The cell culture of claim 1, wherein the culture is capable of at least 6 doublings.

7. The cell culture of claim 1, wherein the cells are derived from the lateral ganglionic eminence (LGE) or medial ganglionic eminence (MGE) of a mammal.

8. The cell culture of claim 1, wherein the doubling rate of the culture is faster than seven days.

9. The cell culture of claim 1, wherein the cells in the culture are murine.

10. The cell culture of claim 1, wherein the cells in the culture are human.

11. The cell culture of claim 1, wherein fewer than 5% of the cells in the culture are β-tubulin III immunoreactive (β-tubulin III$^+$) under proliferation-promoting culture conditions and between 10-40% of the cells in the culture are β-tubulin III immunoreactive (β-tubulin III$^+$) under differentiation-inducing culture conditions.

12. The cell culture of claim 11, wherein the glia are both RC-2$^+$ and vimentin positive.

13. The cell culture of claim 11, wherein the morphology of the glia is:
    (a) bipolar;
    (b) elongated; and
    (c) non-fibrillary.

14. The cell culture of claim 1, wherein the proliferation-inducing growth factor is selected from the group consisting of epidermal growth factor, amphiregulin, basic fibroblast growth factor, acidic fibroblast growth factor, transforming growth factor alpha, leukemia inhibitor factor, ciliary neurotrophic factor and combinations thereof.

15. The cell culture of claim 1, wherein one or more of the cells in culture differentiate into glia in the absence of the proliferation-inducing growth factor from the culture medium.

16. The cell culture of claim 1, wherein one or more of the cells in culture, under differentiation-inducing culture conditions, differentiate into neurons that exhibit:
    (a) axon-dendrite polarity,
    (b) synaptic terminals, and
    (c) localization of proteins involved in synaptogenesis and synaptic activity.

17. The culture of claim 1 wherein the majority of differentiated neuronal cells are immunoreactive with striatal neuronal markers.

18. The culture of claim 1 wherein the majority of differentiated neuronal cells are not immunoreactive with cortical neuronal markers.

19. The culture of claim 1 wherein the majority of differentiated neuronal cells are not immunoreactive with neuronal markers of the medial ganglionic eminence.

20. The cell culture of claim 1, wherein the majority of cells are immunoreactive to RC-2 and nestin.

21. The cell culture of claim 20, wherein the RC-2$^+$ nestin$^+$ cells show glial morphology.

22. The cell culture of claim 1, wherein at least about 75% of cells are immunoreactive to RC-2 and nestin.

23. The cell culture of claim 22, wherein the RC-2$^+$ nestin$^+$ cells show glial morphology.

24. The cell culture of claim 1, wherein at least about 90% of cells are immunoreactive to RC-2 and nestin.

25. The cell culture of claim 24, wherein the RC-2$^+$ nestin$^+$ cells show glial morphology.

26. An in vitro adhesion cell culture of GFAP$^+$ cells, wherein
    a. one or more cells in the culture have the capacity to differentiate into neurons;
    b. the cell culture divides in a culture medium containing serum and at least one proliferation-inducing growth factor; and
    c. one or more cells in the culture differentiate into neurons upon withdrawal of both serum and the proliferation inducing growth factor.

27. The cell culture of claim 26, herein the majority of cells in the culture are nestin$^+$ under proliferation-promoting culture conditions.

* * * * *